(12) United States Patent
Cousins et al.

(10) Patent No.: US 10,779,944 B2
(45) Date of Patent: Sep. 22, 2020

(54) HEART VALVE LEAFLET CAPTURE DEVICE

(71) Applicant: Strait Access Technologies Holdings (Pty) Ltd, Cape Town (ZA)

(72) Inventors: Michael Alan Cousins, Cape Town (ZA); Thomas Gerhardt, Cape Town (ZA); Edward Charles Mudge, Cape Town (ZA); Jeremy Douglas Jarman, Cape Town (ZA); Heather Madeleine Coombes, Cape Town (ZA); Peter Paul Zilla, Cape Town (ZA); Deon Bezuidenhout, Cape Town (ZA)

(73) Assignee: Strait Access Technologies Holdings (Pty) Ltd, Cape Town (ZA)

( * ) Notice: Subject to any disclaimer, the term of this patent is extended or adjusted under 35 U.S.C. 154(b) by 326 days.

(21) Appl. No.: 15/541,570

(22) PCT Filed: Dec. 18, 2015

(86) PCT No.: PCT/IB2015/059785
§ 371 (c)(1),
(2) Date: Jul. 5, 2017

(87) PCT Pub. No.: WO2016/110760
PCT Pub. Date: Jul. 14, 2016

(65) Prior Publication Data
US 2017/0348102 A1 Dec. 7, 2017

(30) Foreign Application Priority Data

Jan. 5, 2015 (ZA) .................................. 2015/00001
Oct. 22, 2015 (ZA) .................................. 2015/07852

(51) Int. Cl.
*A61F 2/24* (2006.01)
*A61B 17/064* (2006.01)
(Continued)

(52) U.S. Cl.
CPC ...... *A61F 2/2463* (2013.01); *A61B 17/00234* (2013.01); *A61B 17/0643* (2013.01);
(Continued)

(58) Field of Classification Search
CPC ...... A61F 2/2466; A61F 2/246; A61F 2/2454; A61F 2/2442; A61F 2/2463; A61F 2/2439; A61F 2/2436; A61F 2/243; A61F 2/2427
See application file for complete search history.

(56) References Cited

U.S. PATENT DOCUMENTS

| 2004/0049207 A1* | 3/2004 | Goldfarb ........... A61M 25/0136 606/139 |
| 2004/0122448 A1 | 6/2004 | Levine |

(Continued)

FOREIGN PATENT DOCUMENTS

| AU | 2002300522 | 1/2007 |
| CN | 103347464 A | 10/2013 |

(Continued)

OTHER PUBLICATIONS

English translation of Search Report dated Jun. 8, 2019 in corresponding Russian Patent Application No. 2017127898.

*Primary Examiner* — Thomas McEvoy
(74) *Attorney, Agent, or Firm* — Cesari and McKenna, LLP

(57) ABSTRACT

The invention provides a heart valve leaflet capture device (250) comprising a cardiac catheter probe having a proximal end for manipulating the device (250) and a distal end terminating in a transvalve element (256). The transvalve element (256) is configured to pass through a heart valve generally parallel to a longitudinal axis of the catheter and includes two or three leaflet gripping elements (252). The leaflet gripping elements (252) are individually movable by operation of an associated actuating mechanism (260)

(Continued)

between a radially retracted position, in which they are withdrawn with respect to the transvalve element (256), and a capture position, in which they diverge outwardly at an acute angle from the transvalve element (256). In the capture position, each leaflet gripping element (252) defines a convergent capture zone that is directed towards the edges of a target valve leaflet and in which the target valve leaflet may be captured.

15 Claims, 18 Drawing Sheets

(51) Int. Cl.
*A61B 17/068* (2006.01)
*A61B 17/128* (2006.01)
*A61B 17/29* (2006.01)
*A61B 17/00* (2006.01)
*A61B 17/122* (2006.01)
*A61B 5/021* (2006.01)
*A61B 90/00* (2016.01)

(52) U.S. Cl.
CPC ........ *A61B 17/0682* (2013.01); *A61B 17/122* (2013.01); *A61B 17/1285* (2013.01); *A61B 17/29* (2013.01); *A61F 2/2466* (2013.01); *A61B 5/021* (2013.01); *A61B 2017/00022* (2013.01); *A61B 2017/00243* (2013.01); *A61B 2017/00309* (2013.01); *A61B 2017/00336* (2013.01); *A61B 2017/00473* (2013.01); *A61B 2017/00783* (2013.01); *A61B 2017/00862* (2013.01); *A61B 2017/2926* (2013.01); *A61B 2090/064* (2016.02); *A61B 2090/065* (2016.02)

(56) References Cited

U.S. PATENT DOCUMENTS

| | | |
|---|---|---|
| 2004/0220593 A1 | 11/2004 | Greenhalgh |
| 2005/0021057 A1 | 1/2005 | St. Goar |
| 2008/0033425 A1* | 2/2008 | Davis ................ A61B 17/0057 606/41 |
| 2012/0253358 A1 | 10/2012 | Golan |
| 2013/0066342 A1 | 3/2013 | Dell et al. |
| 2013/0138121 A1 | 5/2013 | Allen et al. |
| 2014/0222136 A1 | 8/2014 | Geist et al. |
| 2014/0243860 A1 | 8/2014 | Morris et al. |

FOREIGN PATENT DOCUMENTS

| | | |
|---|---|---|
| CN | 103826548 A | 5/2014 |
| RU | 2491035 C2 | 1/2012 |
| WO | WO 2000/003759 | 1/2000 |
| WO | WO-2009080801 A1 | 7/2009 |
| WO | WO-2012/141757 A1 | 10/2012 |
| WO | WO-2013/039804 A1 | 3/2013 |
| WO | WO 2014/138482 | 9/2014 |

* cited by examiner

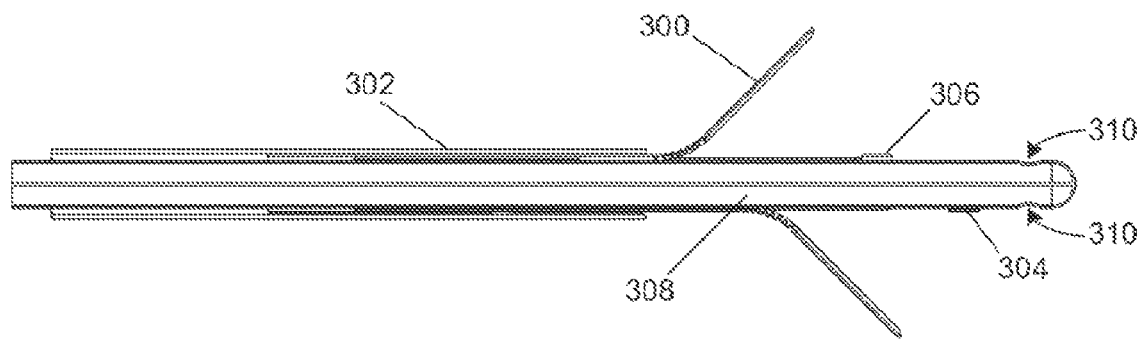
Figure 20
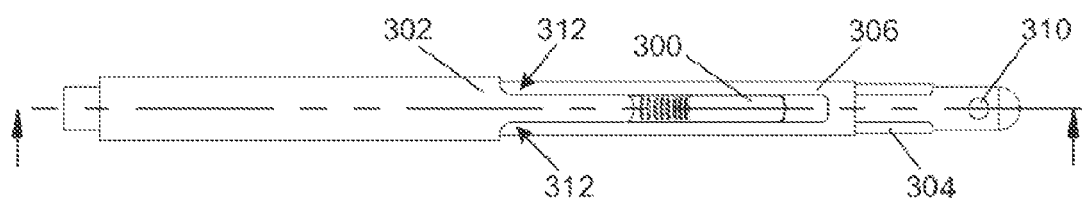
Figure 21
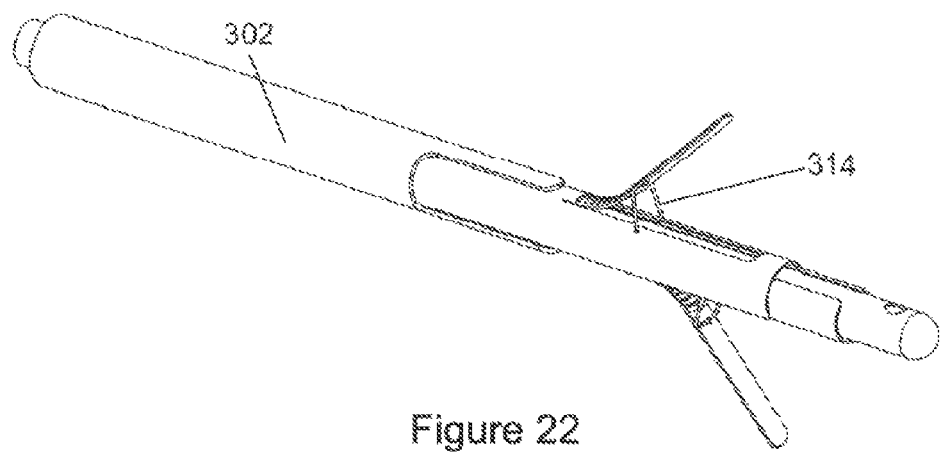
Figure 22
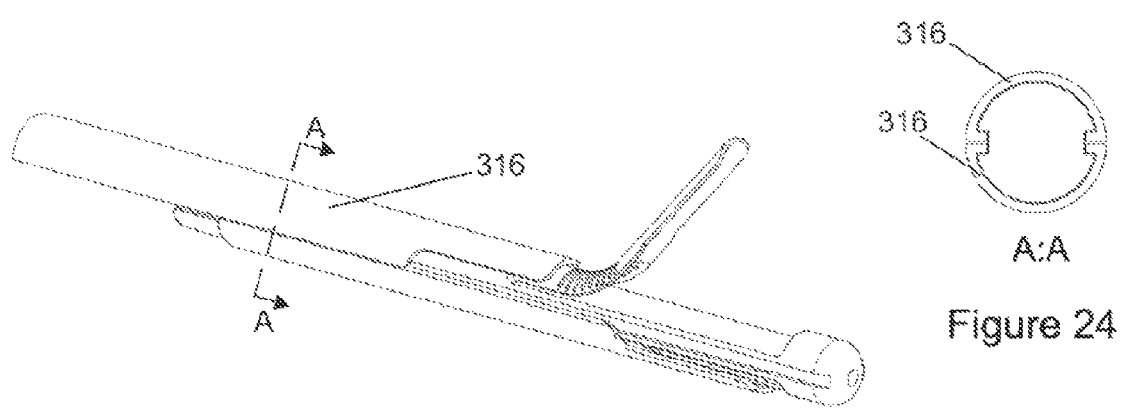
Figure 23
Figure 24

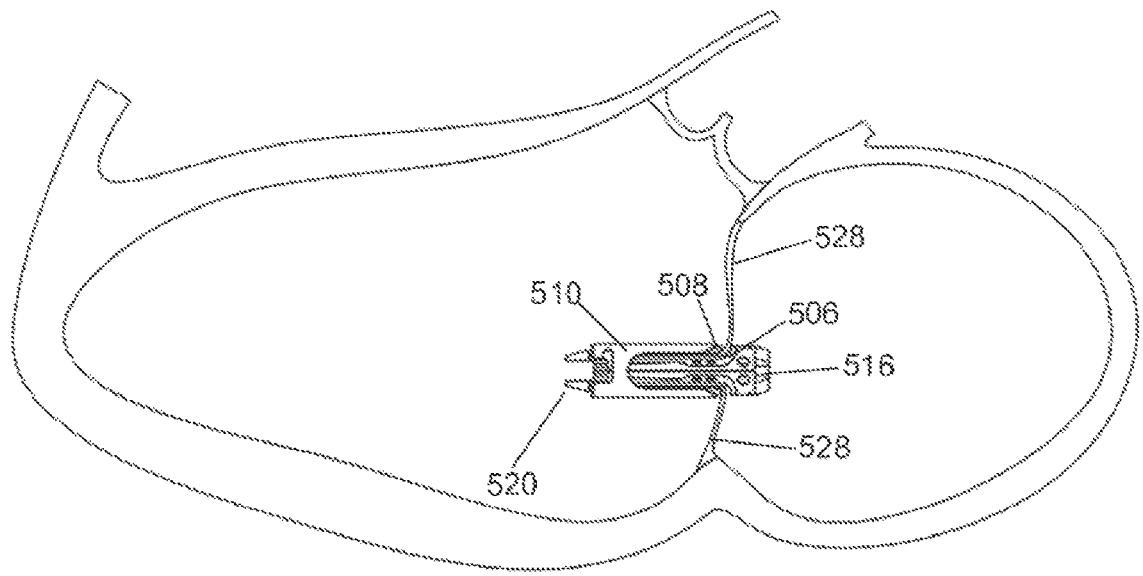
Figure 40
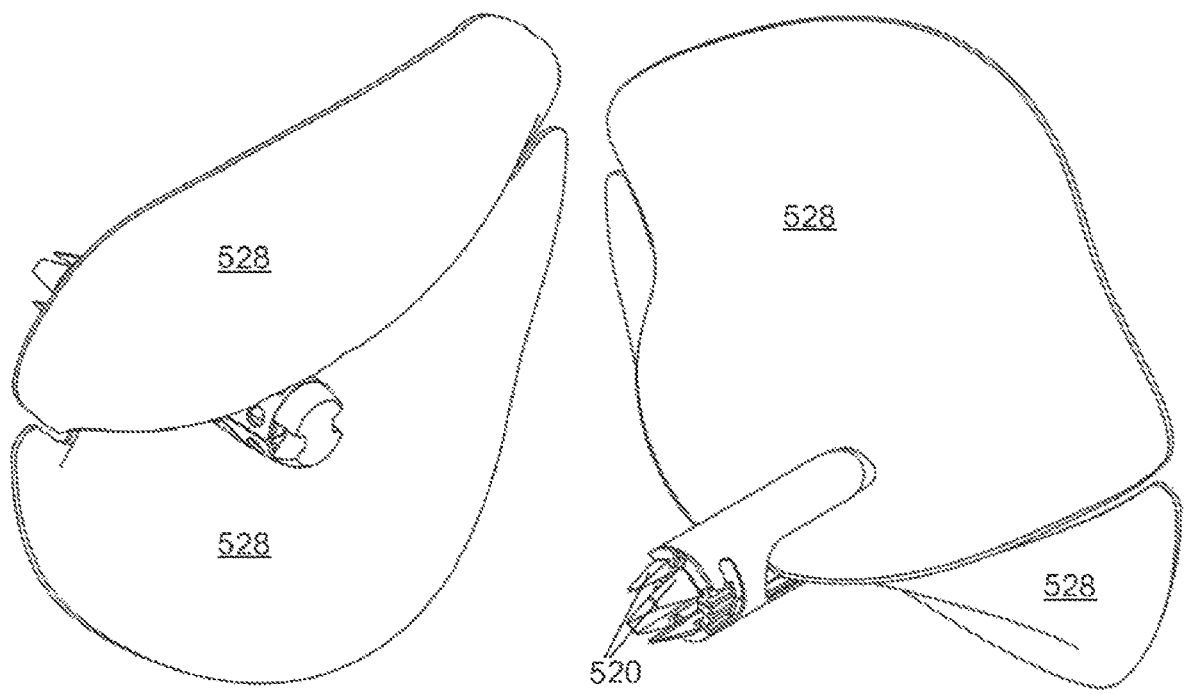
Figure 41
Figure 42

HEART VALVE LEAFLET CAPTURE DEVICE

CROSS REFERENCE TO RELATED APPLICATIONS

This application is the National Stage of International Application No. PCT/IB2015/059785, filed on Dec. 18, 2015, which claims the benefit of South African Application No. 2015/00001, filed on Jan. 5, 2015, and South African Application No. 2015/07852, filed on Oct. 22, 2015. The contents of all prior applications are hereby incorporated by reference in their entirety.

FIELD OF THE INVENTION

This invention relates to a heart valve leaflet capture device for use in conducting percutaneous mitral valve repair procedures and, more particularly to a device for facilitating capture and alignment of the two leaflets of a mitral valve for attachment or fixing to each other to form a more efficient double orifice mitral valve with reduced or eliminated regurgitation. The leaflet capture device is designed to grasp each leaflet of the mitral valve and bring them into a closed position at a point along the line of coaptation. Once each leaflet is captured, the device holds them in apposition so that attachment or fixation of the leaflets to each other can be carried out.

In what follows reference will be made predominantly to mitral valves but it will be understood by those of ordinary skill in the art that the same principles can be applied to other heart valves and devices aimed at such other heart valve are intended to fall within the scope of this invention.

BACKGROUND TO THE INVENTION

The mitral valve in the heart of vertebrate animals is a bicuspid one-way valve situated in the left side of the heart to allow blood to flow in one direction only, namely from the left atrium to the left ventricle. It comprises two leaflets of flexible collagenous material, one anterior and one posterior, which, in normal operation, open as the left ventricle relaxes and dilates (diastole), thereby permitting oxygenated blood originating from the lungs to flow from the left atrium into the left ventricle. The mitral valve is supposed to coapt (close) during the contraction cycle (systole) of the left ventricle to prevent blood from returning to the left atrium. The blood in the left ventricle is forced by the contraction of the left ventricle to flow through the aortic valve and to the rest of the body.

A mitral annulus, which is a fibrous ring having a malformed "D" shape supports the leaflets around their peripheries. The annulus lies in a plane generally perpendicular to the average blood flow direction through the valve. Chordae tendineae are string-like structures which extend between and link papillary muscles on the lower portion of the interior wall of the left ventricle and the free edges of the mitral valve leaflets. These structures prevent the valve from prolapsing into the left atrium during systole.

Mitral valve regurgitation is a common heart condition caused by ineffective closing of the mitral valve generally due to deterioration of the valve itself and/or the surrounding anatomy. Mitral valve regurgitation involves the return flow of blood from the left ventricle back into the left atrium during contraction of the left ventricle. As a result, the left ventricle has to pump harder to circulate blood within it throughout the body. The result is an increase in the risk of congestive heart failure.

Currently a number of percutaneous and surgical mitral valve therapies are available to repair or replace dysfunctional mitral valves. Examples of these procedures are annuloplasty, edge to edge repair, leaflet resection, valvulotomy, valvuloplasty and leaflet plication.

A common approach used to access the mitral valve for percutaneous procedures is through the apex of the heart via a transapical port or by use of purse string sutures, as shown in FIG. 1. An incision is made in the chest wall of a patient and a catheter is advanced through the apex of the heart towards the mitral valve. A number of procedures are based on the surgical Alfieri technique, in which the posterior and anterior leaflets of the mitral valve are joined with a suture or implantable device to create a "double-orifice mitral valve" as shown in FIGS. 2A to 2C. This is aimed at restoring coaptation of the leaflets and thereby reducing or even substantially eliminating mitral regurgitation.

ABBOTT VASCULAR, a current leader in percutaneous edge to edge mitral valve repair, has developed a system in which a steerable catheter is used transseptally to deliver a clip, known as the MitraClip™, to the anterior and posterior leaflets of the mitral valve. A single clip has two grippers that open and close in the manner of a hinged pair of jaws, and the clip is manipulated so that it clips the two mitral valve leaflets together to form a double-orifice mitral valve. Each of the hinged jaws is actuated to an open or closed state simultaneously, as both jaws are linked to the same actuation element. The clip is then left behind as an implant. The problem with the system is that the clinician must risk loss of capture of the first leaflet when attempting to capture the second leaflet. The loss of a captured leaflet increases the time taken to capture both leaflets, and hence the time taken to perform the repair. Also, effective use of the system depends on the availability of costly imaging equipment.

United States patent U.S. Pat. No. 7,559,936 to Levine describes a procedure in which the leaflets of the mitral valve are individually captured sequentially using a variety of different mechanisms that include suction and a mechanical pair of jaws for each leaflet. Applicant is not aware of any commercially available systems flowing from that patent. Nevertheless that patent sets out the problems involved with this type of procedure effectively and its description is included herein by reference.

There is a need for a leaflet capture device that is designed to grasp each leaflet of the mitral valve and bring them into a closed position at a point along the line of coaptation. Once each leaflet is captured, the device holds them in apposition so that attachment or fixation of the leaflets to each other can be carried out.

The preceding discussion of the background to the invention is intended only to facilitate an understanding of the present invention. It should be appreciated that the discussion is not an acknowledgment or admission that any of the material referred to was part of the common general knowledge in the art as at the priority date of the application.

SUMMARY OF THE INVENTION

In accordance with the invention there is provided a heart valve leaflet capture device comprising:

a cardiac catheter having a proximal end for manipulating the device and a distal end terminating in a transvalve element configured to pass through a heart valve generally parallel to a longitudinal axis of the catheter, two or three leaflet gripping elements each of which is individually movable by operation of an associated actuating mechanism between a radially retracted position, in which the leaflet gripping element is withdrawn with respect to the transvalve element, and a capture position, in which the leaflet gripping element diverges outwardly at an acute angle from the transvalve element, wherein the leaflet gripping elements are positioned relative to the transvalve element so that each in its capture position forms a convergent capture zone directed towards the edges of a target valve leaflet.

In one application of the invention, the device is configured to be used in a retrograde procedure, especially a transapical or transaortic procedure. In that instance the leaflet gripping elements are configured to diverge outwardly with the convergent capture zones facing in the direction of the distal end of the transvalve element.

In another application of the invention, the device is configured to be used in an antegrade approach, such as a transseptal procedure that may use standard access routes such as the femoral veins along with standard methods of percutaneous access to the heart with the convergent capture zones facing in the direction of the proximal end of the transvalve element.

Further features of the invention provide for the leaflet gripping elements actuating mechanism to include longitudinally movable buckling elements that may optionally be integrated with an associated leaflet gripping element by virtue of the buckling element being free to buckle laterally to move an associated leaflet gripping element between its radially retracted position and its capture position; in the alternative for the leaflet gripping elements to be configured to naturally adopt the capture position in the absence of any forces being applied thereto in which instance the actuating mechanism may include a longitudinally movable outer sheath engaging the leaflet gripping elements to move them towards their retracted positions; and in the further alternative for the leaflet gripping elements to be configured to naturally adopt the capture position in the absence of any forces being applied thereto in which instance the actuating mechanism may include a flexible tension element selected from a pull wire, a cord and a cable as well as other mechanical means to move the leaflet gripping elements towards their retracted positions.

Still further features of the invention provide for the leaflet gripping elements to be individually pivotally attached to the catheter probe or transvalve element thereof; in the alternative, for the leaflet gripping elements to be attached to the catheter probe or transvalve element thereof by way of a connecting zone that is flexible or deformable; in a further alternative for the leaflet gripping elements to be carried by an elongate buckling element confined to longitudinal movement whilst allowing lateral buckling to take place to move the associated leaflet gripping element between its capture position and its retracted position; for the leaflet gripping elements to be located either at the same axial position along the length of the catheter or at staggered axial positions which configuration is particularly suitable if an outer sheath is being used to move the leaflet gripping elements inwards towards their retracted positions; for at least one and optionally two or more pressure sensor ports to be associated with the catheter so that the pressure exerted on the distal end thereof can be monitored for control purposes and as a guide to a clinician carrying out a cardiac procedure using the device; and for the pressure sensor ports to be slideably connected or axially movable to enable their use for assessing atrio-venticular position or for assessing leaflet position relative to the capture and fixation device and successful leaflet capture by the leaflet gripping elements of the device.

Yet further features of the invention provide for the catheter to have a longitudinal slider associated with each of the leaflet gripping elements so that their positions along the length of the transvalve element or catheter can be adjusted as may be required; in the alternative, for the catheter and transvalve element to be longitudinally split into two or more longitudinally adjustable parts that can be moved in order to effectively capture heart valve leaflets or to align captured leaflets into a desired relative position; and for the gripping surfaces of the leaflet gripping elements to be provided with barbs, spikes or other projections for releasably attaching the leaflet gripping element to a heart valve leaflet with which it is brought into contact; and for the leaflet gripping element to be releasable from the catheter or transvalve element.

Further features of the invention provide for the device to include two or three atrial stoppers, each being associated with a leaflet gripping element and being individually movable between an inoperative configuration, in which the stopper locates generally adjacent the transvalve element, and an operative configuration, in which the stopper diverges outwardly at an acute angle from the transvalve element so as to, in use, capture a valve leaflet between the stopper and the associated leaflet gripping element; for each atrial stopper to be pivotally attached to the catheter probe or transvalve element thereof; for each atrial stopper to be movable between the inoperative configuration and the operative configuration by operation of an associated operating mechanism; for the operating mechanism to include longitudinally movable operating members that may be integrated with an associated stopper and which are free to bend laterally so as to move an associated stopper between its inoperative configuration and its operative configuration; alternative for the stopper to be configured to naturally adopt the operative configuration in the absence of any forces being applied thereto in which instance the operating mechanism may include a flexible tension element selected from a pull wire, a cord and a cable as well as other mechanical means to move the stopper towards its inoperative configuration; further alternatively for the stopper to be configured to naturally adopt the inoperative configuration and for the operating mechanism to include a flexible tension element to move the stopper toward its operative configuration.

Still further features of the invention provide for the device to be capable of fixing two or more captured valve leaflets relative to one another. In one embodiment, the device includes a piercing element that is held within the distal end of the transvalve element, the piercing element comprising a base from which extend one or more piercing members which are configured to pierce one or more captured leaflets so as to fix the leaflets relative to one another. In an alternative embodiment, the transvalve element is disengageable from the catheter probe so as to, in use, disengage the transvalve element from the probe to remain in position once the two or more leaflets have been captured and brought into apposition thereby fixing the captured leaflets relative to one another.

In order that the above and other features of the invention may be more fully understood various embodiments of the invention will now be described with reference to the accompanying drawings.

BRIEF DESCRIPTION OF THE DRAWINGS

In the drawings:

FIG. 16 is a three-dimensional view from the posterior and distal side of a further embodiment of a heart valve leaflet capture device in which two parts of the probe can slide relative to each other to adjust longitudinal position of the leaflet gripping elements;

FIG. 20 is a sectional view of a further embodiment of a heart valve leaflet capture device in which the leaflet gripping elements naturally adopt the capture position and the device includes an axially slideable sheath for moving the gripping elements from the capture position to the retracted position;

FIG. 21 is a plan view of the device shown in FIG. 20;

FIG. 22 is a three-dimensional view of a further embodiment of a heart valve leaflet capture device similar to the device shown in FIG. 20, provided that in this embodiment the device further includes tension elements to move the gripping elements to the retracted position;

FIG. 23 is a three-dimensional view of a further embodiment of a heart valve leaflet capture device in which one diametric half of the outer sheath for closing the leaflet gripping elements is axially movable relative to the other;

FIG. 24 is a cross-section of the device shown in FIG. 23 along the line A:A;

FIG. 37A to 37C are a series of plan views showing the procedure of disengagement of the transvalve element from the catheter probe;

FIG. 40 is a diagrammatic sectional view of the human heart showing the transvalve element of the device shown in FIG. 34 being used to fix the two mitral valve leaflets relative to one another;

FIG. 41 is a three-dimensional view from the posterior and distal side of the disengaged transvalve element shown in FIG. 40;

FIG. 42 is a three-dimensional view from the anterior and proximal side of the disengaged transvalve element shown in FIG. 40;

DETAILED DESCRIPTION WITH REFERENCE TO THE DRAWINGS

Figure 1:
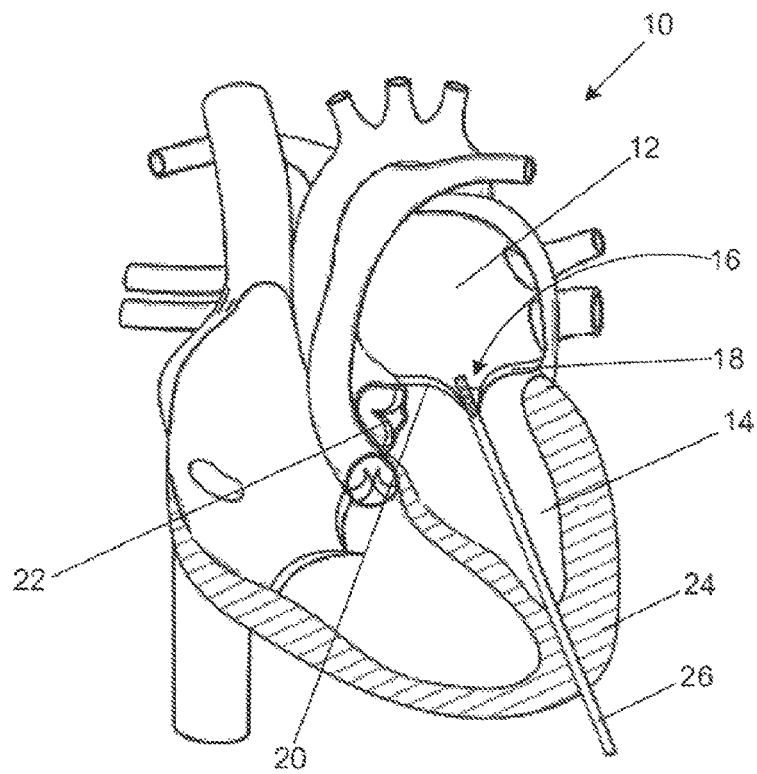
FIG. 1 is a diagrammatic sectional view of the human heart showing the mitral and aortic valves and a device according to the invention in association therewith with reference to one possible access route to the mitral valve, showing the device used with transapical access.
Figure 2A:
FIGS. 2A to 2C are schematic surgeon's views of, respectively, a normal mitral valve in the open condition; a normal mitral valve in the closed condition; and a mitral valve after an edge to edge type of repair procedure has been performed on it.
Figure 2B:
Figure 2C:

FIG. 1 of the drawings illustrates the human heart (10) having a left atrium (12) and a left ventricle (14) interconnected by a mitral valve (16) having a posterior leaflet (18) and an anterior leaflet (20) and with an aortic valve (22) as an outlet from the left ventricle (14).

The left ventricle (14) is accessible for a retrograde transapical procedure by way of the apex (24) of the heart (10), in known manner by a device (26) according to the invention. Of course, in another embodiment, the device according to the invention may also be used for an antegrade access procedure by way of the left atrium as is known in the art.

Figure 3:
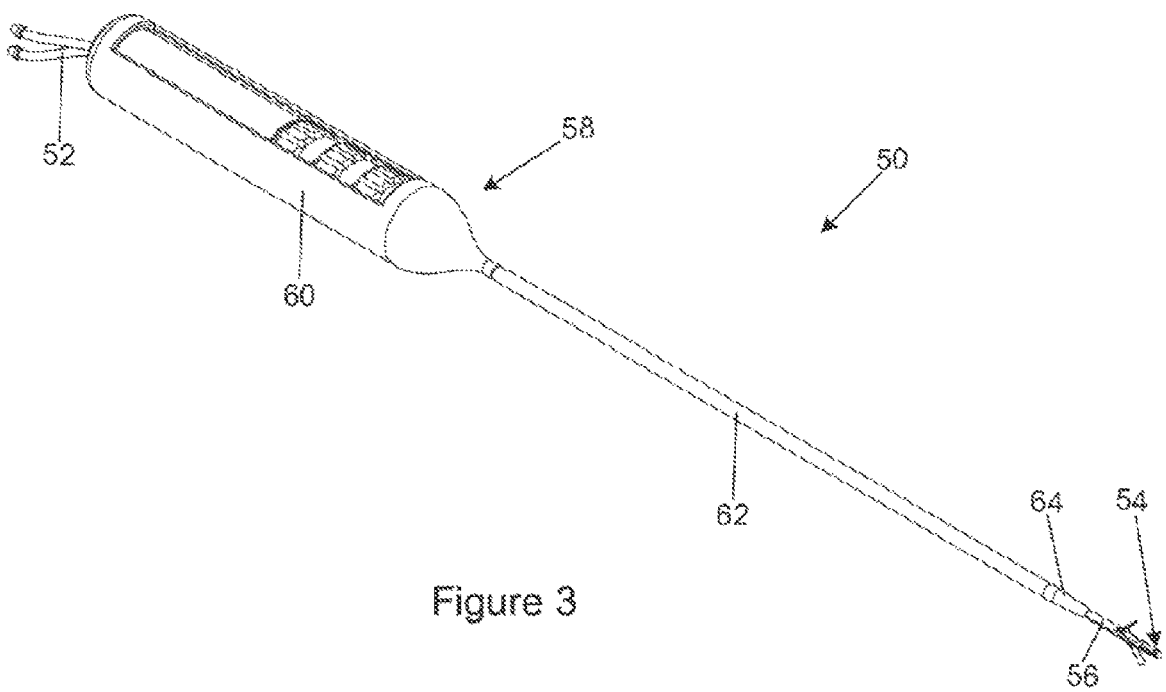
FIG. 3 is a three-dimensional view of a complete cardiac catheter assembly fitted with the device according to the invention.
Figure 4:
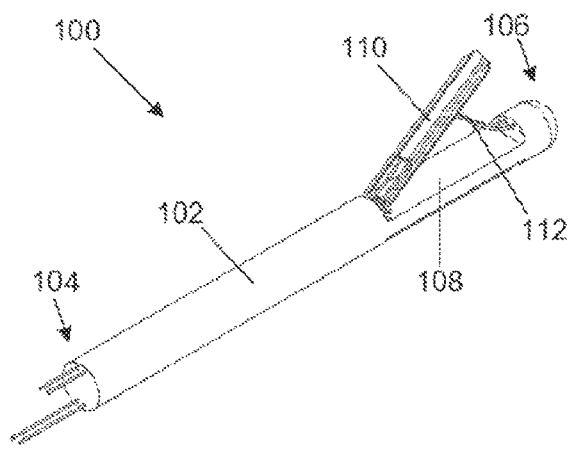
FIG. 4 is a three-dimensional view of one embodiment of a heart valve leaflet capture device according to the invention from a proximal end region thereof, with the anterior leaflet gripping element in its capture position.
Figure 5:
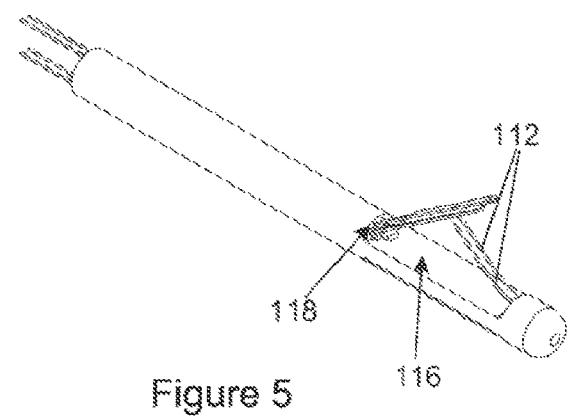
FIG. 5 is a three-dimensional view of the device of FIG. 4 but from a distal end region thereof.
Figure 6:
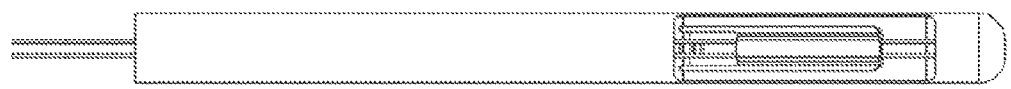
FIG. 6 is a top view of the device of FIG. 4.

Simply for the sake of completeness, a complete cardiac catheter assembly (50) in accordance with the invention is illustrated in FIG. 3. In this instance, pressure lines (52) are provided for connecting a transducer (not shown) to pressure sensing ports (54) within the probe (56) of the invention. The proximal end (58) of the assembly (50) has an actuating element in the form of a handle (60) or other clinician interface. The transmission or delivery catheter system (62) could be rigid, curved, bendy flexible or steerable and configured to be insertable into a patient's heart through appropriate access routes such as the apex of the heart, or transseptally or by means of a transfemoral access route.

The probe (56) is housed within a housing element (64) which may assist in positioning the probe (56) correctly with respect to the surrounding anatomy of the heart. In the embodiment illustrated in FIG. 3, the housing element (64) is steerable through manipulation and/or actuation of the handle (60) so as to correctly position the probe with respect to the surrounding anatomy. In an alternative embodiment, the housing element may be a mechanical anchoring system configured to position the capture device or probe (56) relative to specific surrounding anatomy by making contact with specific parts of the surrounding anatomy.

Figure 7:
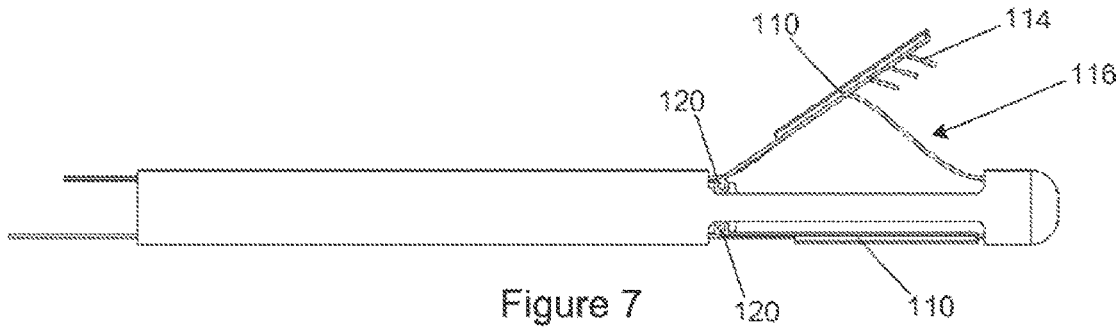
FIG. 7 is a side view of a further embodiment of a heart valve leaflet capture device which is substantially similar to the device of FIG. 4, but in which the leaflet gripping elements include barbs or spikes.
Figure 8:
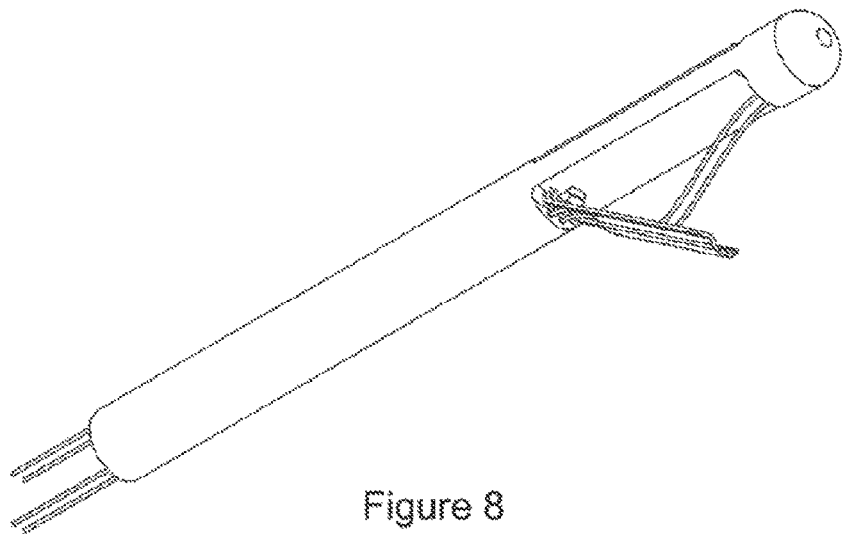
FIG. 8 is a three-dimensional view from the underside of the device of FIG. 4 showing the posterior leaflet gripping element in its capture position.

FIGS. 4 to 8 illustrate one embodiment of a leaflet capture device (100) in accordance with the invention. The device (100) comprises a cardiac catheter in the form of a probe (102) having a proximal end (104), and a distal end (106) terminating in a transvalve element (108) configured to pass through a heart valve, in this embodiment the mitral valve, who's annular plane is generally normal to a longitudinal axis of the catheter. The transvalve element (108) has two leaflet gripping elements (110) each of which is individually movable by operation of an associated actuating mechanism, which in this embodiment includes a pair of longitudinally movable buckling elements (112), between a radially retracted position, as shown in the lower of posterior half of FIG. 7 in which it is withdrawn with respect to the transvalve element (108), and a capture position, as shown in the upper or anterior half of FIG. 7 in which it diverges outwardly at an acute angle from the transvalve element (108). In addition and as shown in FIG. 7, the leaflet gripping elements (110) may be provided with inwardly directed barbs or spikes (114) designed to ensure that the gripping element (110) remain engaged when desired. The barbs (114) are preferably designed to have an angle of contact with the leaflets such that they may release the leaflets when desired. It will of course be appreciated that the presence or absence of such barbs will depend on the exact service to be performed by the device (100).

In the embodiment illustrated, the two leaflet gripping elements (110) are positioned on diametrically opposite sides of the transvalve element (108) so that each in its capture position forms a convergent capture zone (116) directed towards the edge of the valve leaflets.

Figure 9:
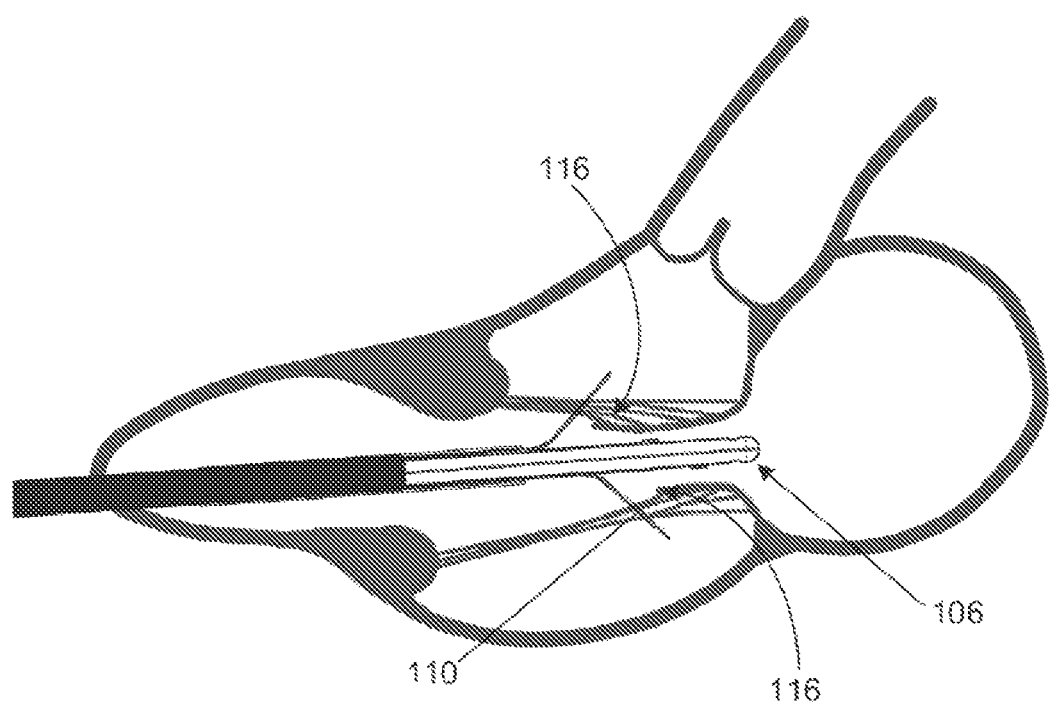
FIG. 9 is a diagrammatic sectional view of the human heart showing retrograde access to the mitral valve by way of transapical access through the apex of the heart and the left ventricle.

The direction in which the leaflet gripping elements extend in the capture position will depend on the type of procedure in which the device is to be used. Thus, in the instance illustrated in FIG. 9, the mitral valve leaflet capture device is configured to be used in a retrograde procedure such as a transapical or transaortic procedure and in which case the convergent capture zone formed (116) by the leaflet gripping elements (110) is directed toward the distal end (106) of the device with the pivoting or bending region of the grippers is positioned nearer the proximal end of the device.

Figure 10:
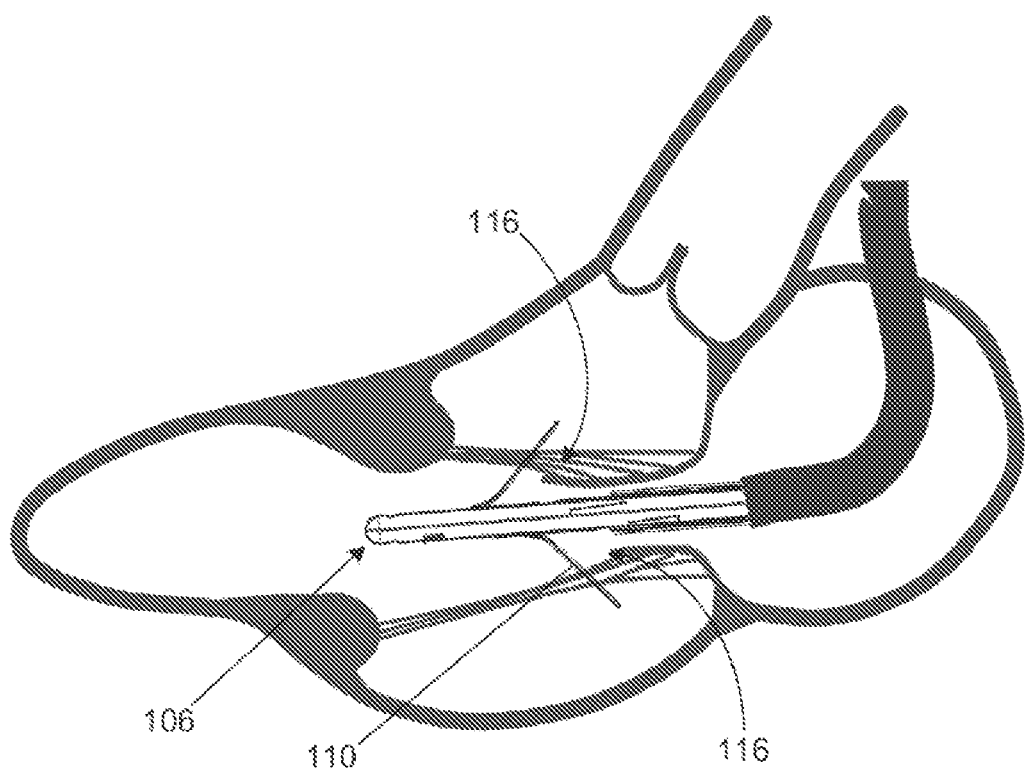
FIG. 10 is a diagrammatic sectional view of the human heart showing antegrade access to the mitral valve by way of the left atrium.

On the other hand, if the device is to be used in an antegrade procedure, as shown in FIG. 10, such as a transseptal procedure for example using standard access routes such as the femoral veins along with standard methods of percutaneous access to the left atrium via the intra-atrial septum or a transatrial procedure, then the leaflet gripping elements (110) would be directed in the opposite direction with respect to the transvalve element or distal end (106) of the device, but in the same direction with respect to the heart valve when correctly orientated within the heart, as will be perfectly apparent to one of ordinary skill in the art.

In the embodiment illustrated in FIGS. 4 to 8, the pair of longitudinally movable buckling elements (112) are in the form of wires that may have a circular, square, oval, rectangular or other polygonal cross-sectional shape that may vary along the length of the element (112). The buckling elements (112) are longitudinally movable from the proximal end (104) of the catheter (102) and are constrained so that they are free to buckle laterally outwards under sufficient compressive load to move an associated leaflet gripping element (110) between its radially retracted position and its capture position. The buckling elements (112) may be fed or woven through holes (118) in the transvalve element (108) and in the leaflet gripping elements (110), such that the buckling elements (112) locate the leaflet gripping elements (110) relative to the transvalve element (108).

Furthermore, in the embodiment illustrated, the leaflet gripping elements (110) are attached to the transvalve element (108) by pivots (120) approximately at a position where the leaflet gripping elements (110) join the transvalve element (108) so that they are freely movable between the retracted position and the capture position. Accordingly, the leaflet gripping elements (110) are constrained to move angularly to follow the laterally movable portions of the buckling elements (112) to which they are attached approximately midway along the length of the leaflet gripping elements (110). It is anticipated that the buckling elements (112) can be made from super-elastic/shape-memory alloy such as nitinol or other material having similar properties.

FIGS. 11A to 11H illustrate a sequence of stages of capture of the two leaflets (150, 152) of a mitral valves (154) using one embodiment of a leaflet capture device (156) in accordance with the invention. The Figures show the ability of the leaflet gripping elements (158) to be individually opened and closed, or moved from the capture position to the retracted position and vice versa. In addition, in the embodiment illustrated, the leaflet gripping elements (158) are capable of being moved in an axial direction individually. It will be appreciated the individual movement of the gripping elements (158) will enable individual leaflet capture and to then bring the captured leaflets into apposition prior to fixation thereof relative to each other.

Figures 11A, 11B:
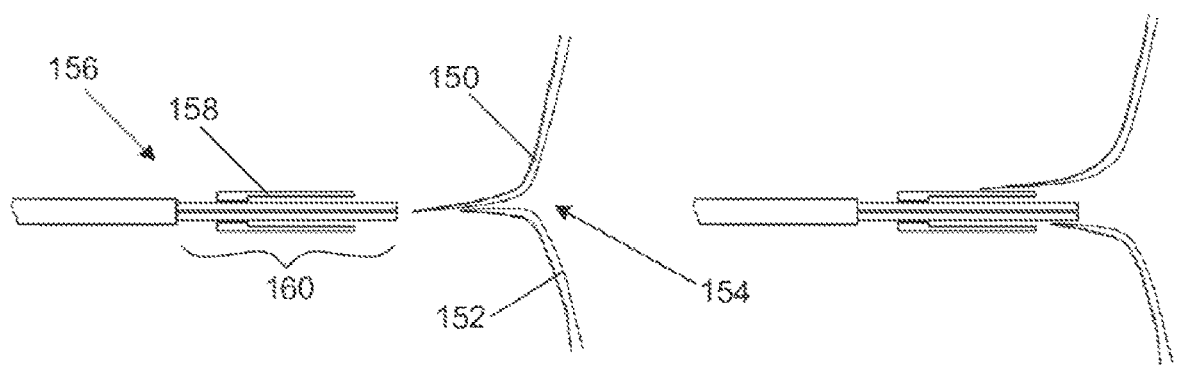
FIG. 11 schematically shows in a succession of FIGS. 11A through 11H the various stages of capture of the two leaflets of a mitral valve.
Figures 11C, 11D:
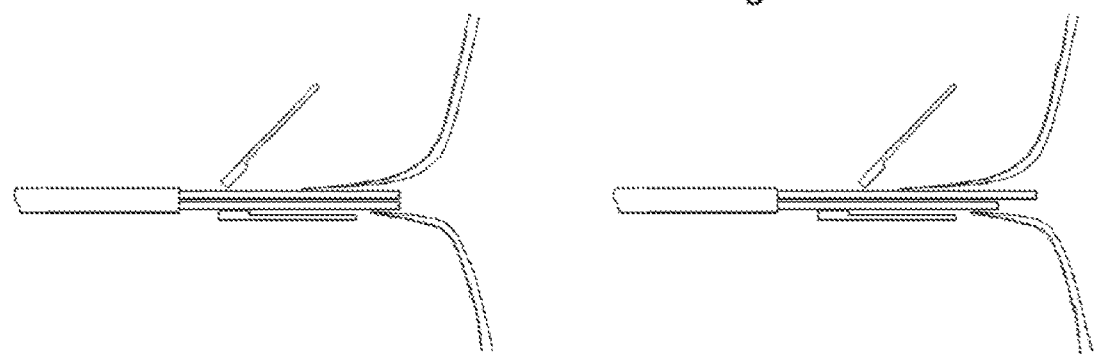
Figures 11E, 11F:
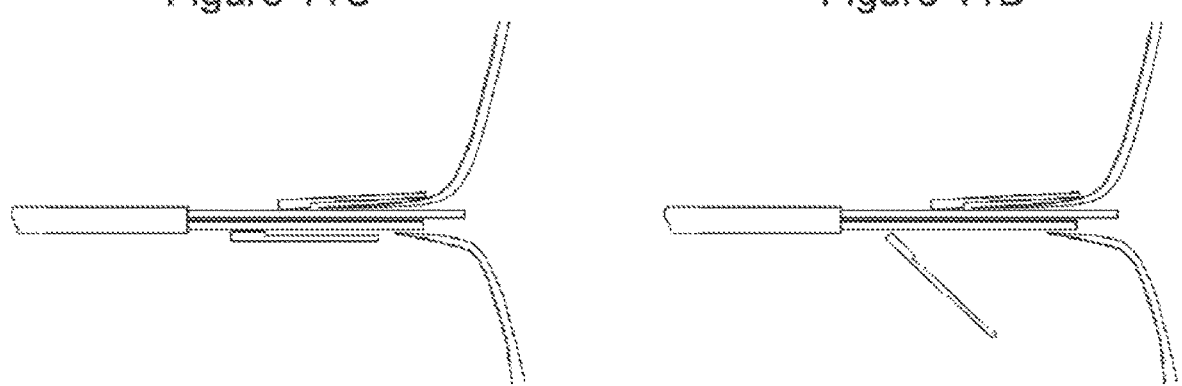
Figures 11G, 11H:
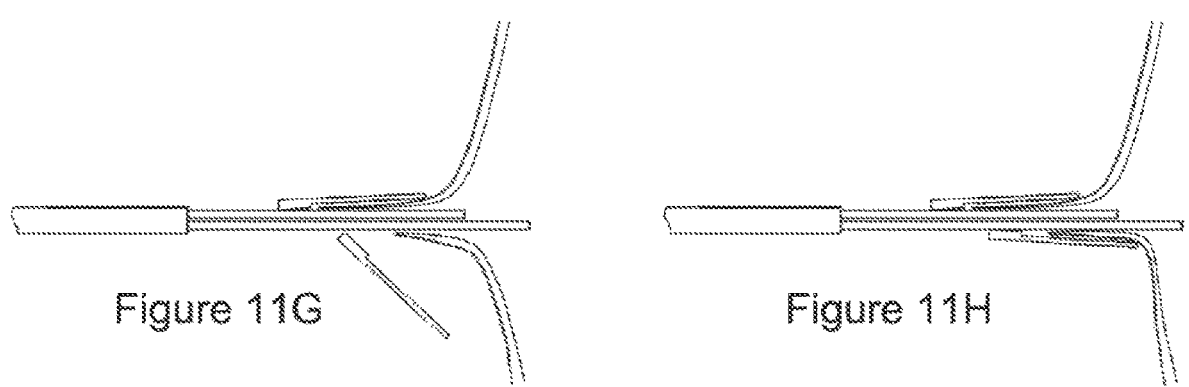

In FIGS. 11A and 11B, both leaflet gripping elements (158) are in the retracted position, in which they are withdrawn with respect to the transvalve element (160) so that the probe (162) is roughly tubular during the approach to the two leaflets (150, 152) of the mitral valve (154). As shown in FIGS. 11C to 11E, one of the leaflet gripping elements (158), in this case the anterior leaflet gripping element, may be opened to its capture position with the other gripping element (158) remaining in its retracted position. Since the gripping elements (158) are capable of axially being moved independently of each other, the anterior leaflet gripping element may be moved so as to be better positioned with respect to the anterior leaflet (150) and such that it may then be actuated to its retracted position, as shown in FIG. 11E, thereby capturing the leaflet (150). Once a leaflet has been captured, in this case the anterior leaflet (150), then the second leaflet gripping element (158) is moved to its leaflet capture position as shown in FIG. 11F. FIGS. 11F to 11H are similar to FIGS. 11C to 11E, except that in this case the posterior leaflet (152) is captured. In addition, prior to capturing of the posterior leaflet (152), the posterior leaflet gripping element (158) is moved axially so as to ensure that the leaflet (152) is captured in a position that is suitable relative to the anterior leaflet (150).

A condition that is predominant in diseased or pathological valves, but may also occur naturally, is that the free edge of the mitral valve leaflets align at the same distance from the mitral annulus and it may be the case that the anterior leaflet is slightly longer than the posterior leaflet, thus extending further away from the mitral plane or annulus. For this reason, it is essential that the two gripping elements of the device can be individually moved axially relative to the probe.

It will of course be appreciated that irrespective of the procedure followed, thus whether retrograde or antegrade, the procedure of capturing a leaflet will be the same as described above. A further alternative approach would be to pass the device through the Aortic valve, make a sharp turn within the left ventricle and then proceed through the mitral valve. In this instance, access routes such as the femoral arteries could be used.

Figure 12:
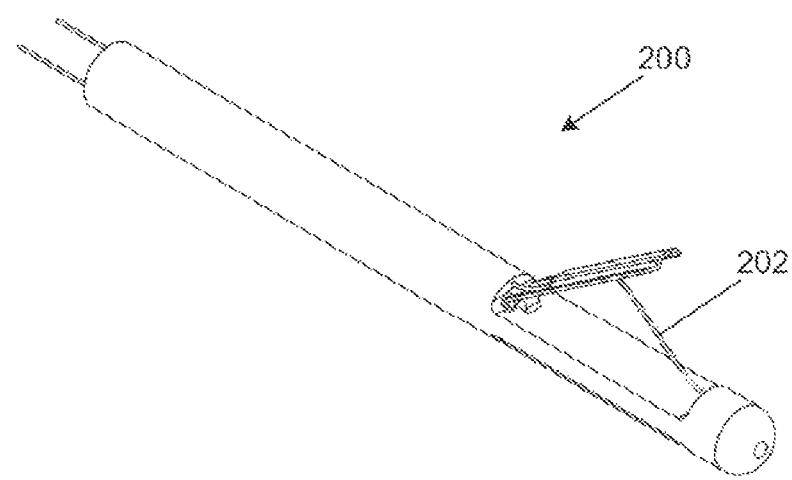
FIG. 12 is a three-dimensional view of a simplified embodiment of the heart valve leaflet capture device shown in FIGS. 4 to 8.

FIG. 12 illustrates a further embodiment of a leaflet capture device (200) in accordance with the invention, in which the buckling element (202) assumes the form of a single wire.

Figure 13:
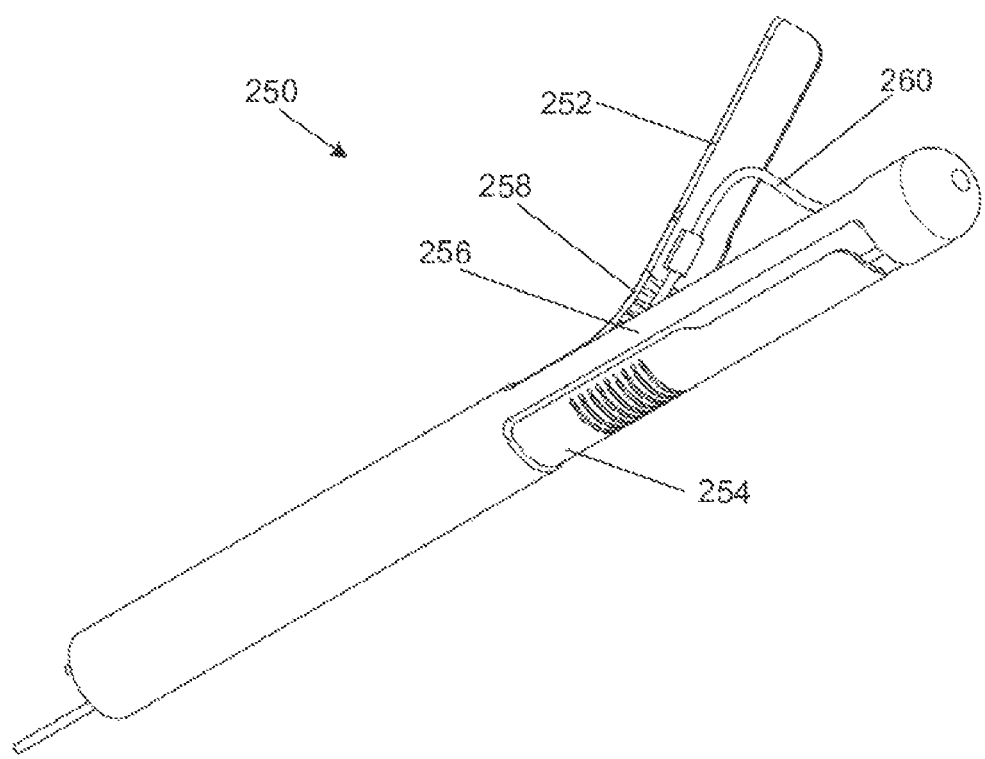
FIG. 13 is a three-dimensional view from the posterior and distal side of a further embodiment of a heart valve leaflet capture device.
Figure 14:
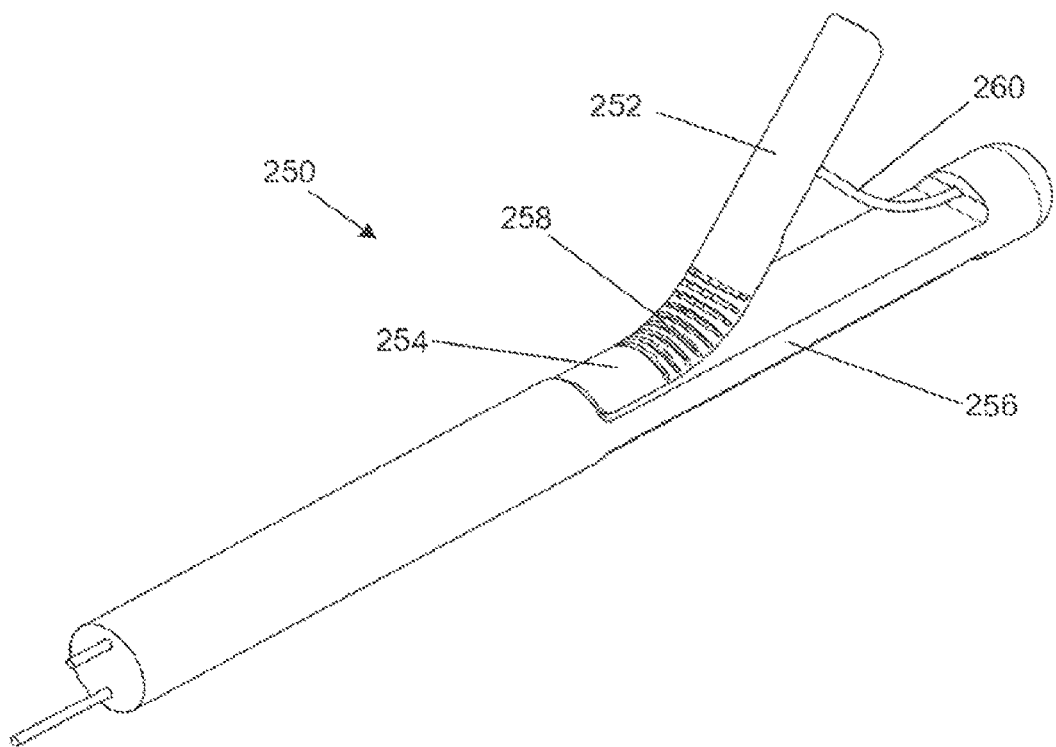
FIG. 14 is a three-dimensional view from the anterior and proximal side of the device shown in FIG. 13.
Figure 15:
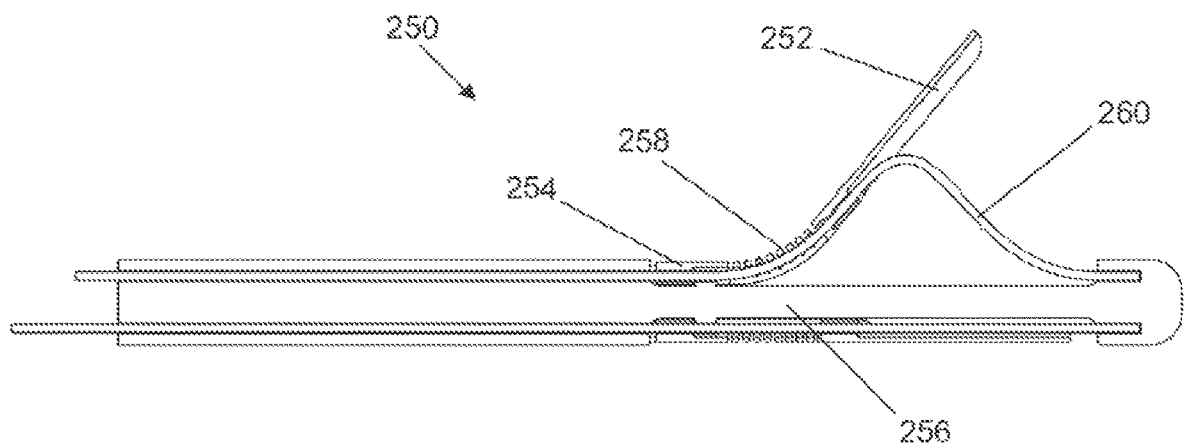
FIG. 15 is a section view of the device shown in FIGS. 13 and 14.

FIGS. 13 to 15 illustrate yet a further embodiment of a leaflet capture device (250) in accordance with the invention. In this embodiment, the leaflet gripping elements (252) are connected to a part (254), also referred to as a living hinge, that is fixed relative to the transvalve element (256) by an integral connecting zone (258) that is flexible or deformable by virtue of the material being slotted, grooved or otherwise configured to enable the leaflet gripping elements (252) to move between their retracted positions and their capture positions. The buckling element (260) shown is in the form of a single wire but any other suitable buckling element may be used, for example two wires or the like.

It will be advantageous for the capture device to be able to capture each leaflet at the correct distance from the mitral plane or annulus that is specific to each leaflet. By the same token, it may be more advantageous to independently move a leaflet after it has been captured. This may be necessary for prolapsing leaflets that have been captured in a position that is suboptimal for repair and where moving such a leaflet axially with respect to the other leaflet post capture would improve valve coaptation. Once leaflets have been aligned to an optimal position axially with respect to one another and/or with respect to the mitral plane or annulus, a repair can be carried out. Independent axial actuation of each leaflet gripping element may be achieved by mounting it to a slider or movable element as illustrated in FIGS. 17 to 19.

In addition, since the device enables movement of the captured leaflets relative to one another, the optimal alignment position of the leaflets may be determined prior to performing the repair procedure. Thus, prior to performing the repair procedure, the captured leaflets may be moved relative to one another and by using known methods, such as echocardiography, fluoroscopy, pressure differentials and the like, the optimal alignment position of the leaflet can be determined. Once the optimal position has been determined, the repair procedure may be performed so as to maintain the leaflets at the determined optimal position.

Figure 17:
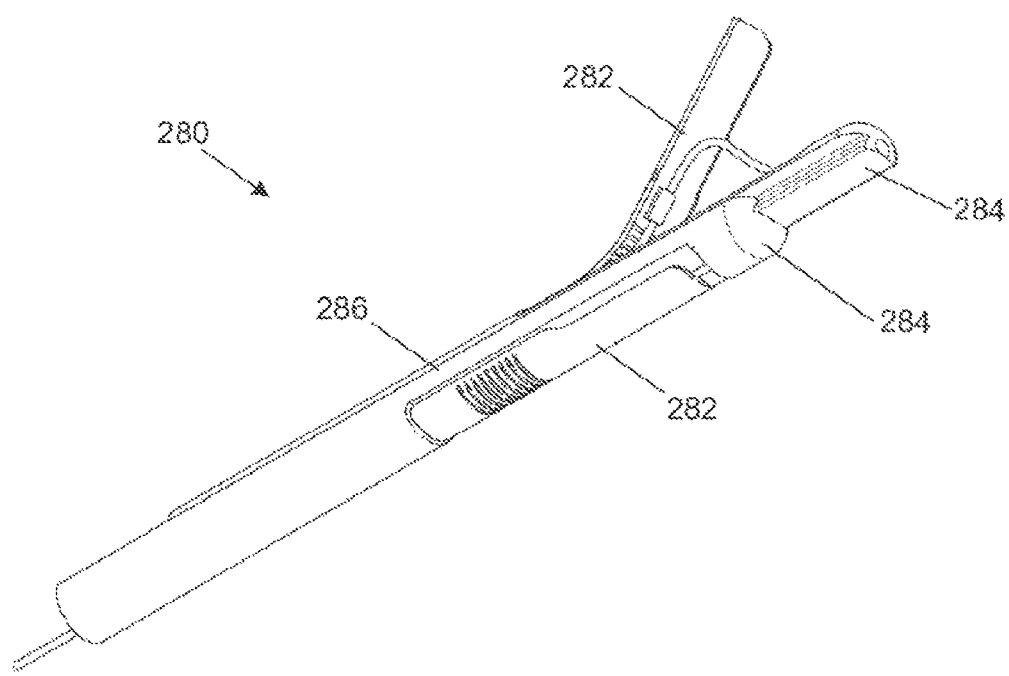
FIG. 17 is an end view of the device shown in FIG. 16 with both leaflet gripping elements in their retracted position.
Figure 18:
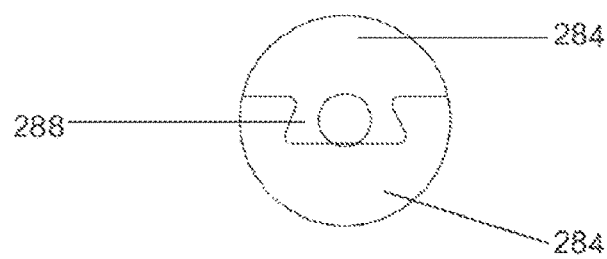
FIG. 18 is a side view of the device shown in FIG. 16.
Figure 19:
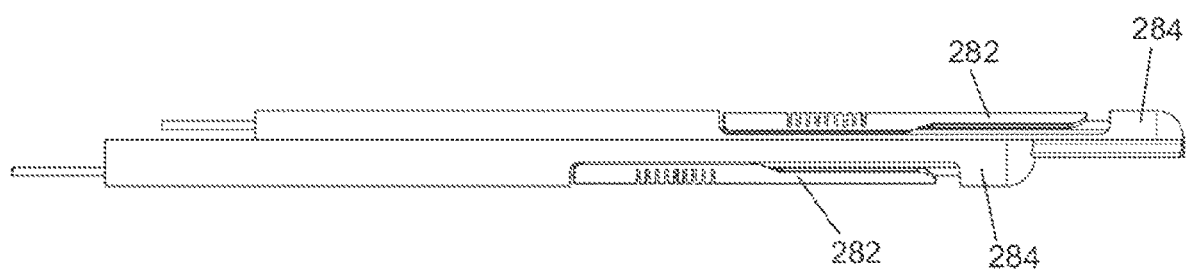

FIGS. 17 to 19 illustrate such a further embodiment of a leaflet capture device (280) in which the leaflet gripping elements (282) are each carried on a separate longitudinally movable half part (284) or slider of the probe (286) so that the longitudinal positions of the two leaflet gripping elements (282) relative to each other can be adjusted as may be required in order to position the required part of one of the mitral valve leaflets relative to the other. As shown in FIG. 18, the interconnection could be a dovetail type of cross-sectional shape (288) permitting of relative longitudinal movement of the two parts (284). It will be appreciated that by moving a half part (284) or slider in an axial direction, one may reposition the leaflet gripping element (282) axially to the correct depth for capture of a leaflet. Alternatively, once the leaflets have been captured, the sliders may be moved axially so as to position the leaflets relative to each other prior to fixation thereof. Because each slider can move axially independently of the other, it is possible to move each leaflet gripping element in an axial direction independently of the other.

The leaflet gripping elements (300) may of course also be configured to adopt the capture position as their natural position in the absence of any forces being applied thereto, as best illustrated in FIGS. 20 to 21. In this case, the actuating mechanism may include a longitudinally movable outer sheath (302) which engages the leaflet gripping elements (300) so as to move them against the natural bias from the capture position towards their retracted positions. In order to enable the leaflet gripping elements (300) to be activated individually, the leaflet gripping elements (300) are provided on separate sheaths (304, 306), the one sheath (304) sliding within the other sheath (306). This enables the leaflet gripping elements (300) to be moved axially relative to one another so as to stagger them along the length of the transvalve element (308). This permits the first one to be engaged in the first instance by a predetermined movement of the outer sheath (302) on the outside surface of the probe and the second one is engaged subsequently consequent on further movement of the outer sheath (302). In between consecutive engagement of the leaflet gripping elements by the sheath, appropriate manipulation may be carried out to adjust the positions of the leaflet gripping elements relative to each other and independent re-positioning of captured leaflets may also be achieved.

In addition, FIGS. 20 and 21 illustrate that two separate pressure sensing ports (310) may be provided, one on the anterior side of the transvalve element (308) and the other on the opposite side thereof. The use of pressure sensing ports (310) will permit the device to be used without necessarily requiring sophisticated imaging apparatus and it is envisaged that monitoring the pressure exerted onto the distal end of the probe by way of the ports (310) be all that is required due to the pressure differences in the left ventricle and left atrium and the ability to monitor leaflet positions using pressure. In addition, the ports could be used to determine whether the device has been properly located within the valve such that the leaflets will close their respective ports during closing of the valve thereby causing a change in pressure to be measured. This will be described in more detail further below. Also, one or both of the ports could be used to apply a vacuum to a leaflet should the convenience therefore be present.

It is important to note that where a sliding sheath is used, a suitable cut out (312) needs to be provided in the sheath so as to accommodate the leaflets once captured.

It will of course be appreciated that in order to assist or instead of the outer sheath (302), a tension element such as a pull wire (314), as illustrated in FIG. 22, may be provided to move the leaflet gripping elements toward their retracted positions.

In still a further alternative embodiment and as illustrated in FIG. 23, the probe could have a longitudinally slidable outer half sheath (316) on each side of the probe so that by longitudinal movement of the half sheath the leaflet gripping elements can be operated independently of each other. In this regard, FIG. 24 illustrates one possible method of slidably connecting the two outer half sheaths (316) with the central probe or transvalve element.

Figure 25:
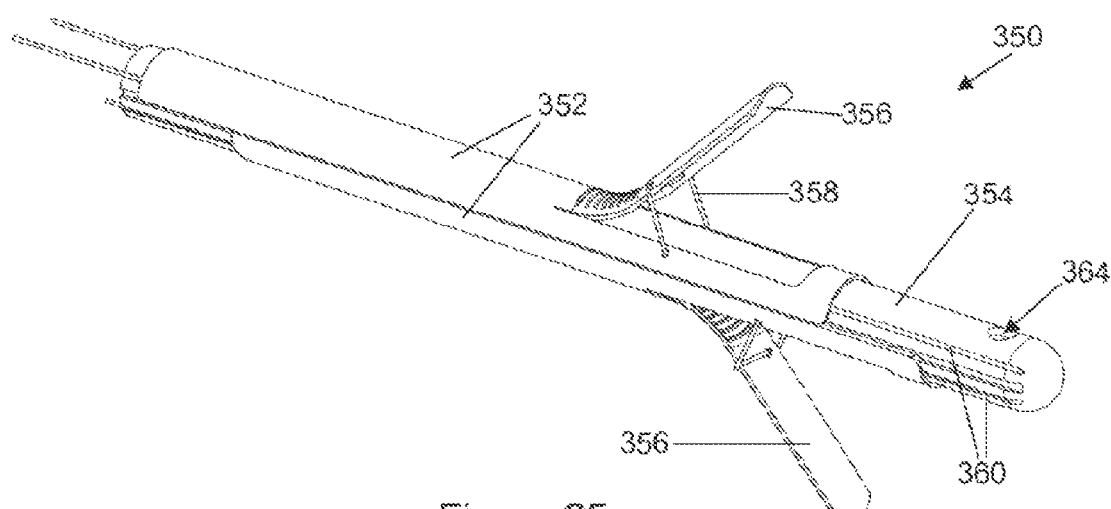
FIG. 25 is a three-dimensional view of a further embodiment of a heart valve leaflet capture device in which the device includes two diametrically opposing sliders that are axially movable relative to one another and the leaflet gripping elements extend from the sliders.
Figure 26:
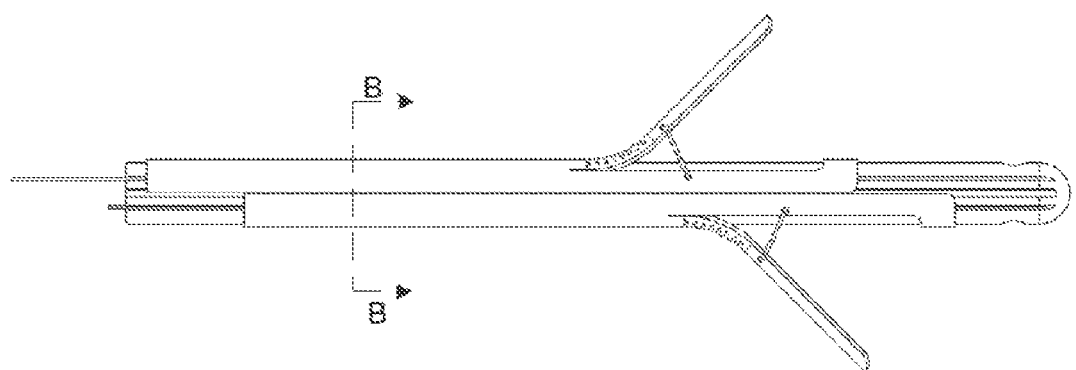
FIG. 26 is a side view of the device shown in FIG. 25.
Figure 27:
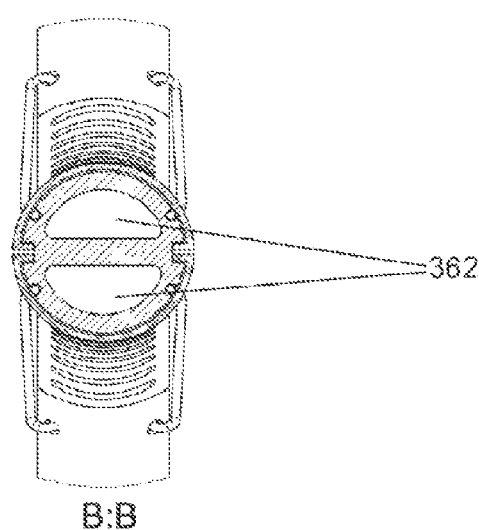
FIG. 27 is a cross-section of the device shown in FIG. 26 along the line B:B.

FIGS. 25 to 27 illustrate yet a further embodiment of a leaflet capture device (350) in accordance with the invention. In this embodiment, similar to the embodiment of FIGS. 23 and 24, the device (350) has two separate longitudinally slidable sliders (352) connected to the probe (354), with a leaflet gripping element (356) extending from each slider (352). In this embodiment, the leaflet gripping elements (356) have a natural capture position and are moved to the retracted position by means of flexible tension elements (358). The tension elements (358) may be confined in the longitudinal direction in grooves (360) provided in the outer surface of the probe (354) and within the sliders (352). In addition, the device (350) further includes two parallel lumens (362) which communicate with a port (364) provided on either side at the distal end of the probe (354). The lumens (362) may, as described above, be used for either pressure sensors or for a vacuum and/or suction arrangement.

It will be appreciated that the two pressure sensing ports (310, 364) and parallel lumens (362) of FIGS. 20 to 21 and 25 to 27 may further function as part of a leaflet capture confirmation system. In one embodiment, the system may include transducers and monitors external to the patient and provides the clinician with pressure feedback in the form of real time wave like pressure signals displayed on a screen or monitor. For example, by positioning the pressure sensing ports such that they lie axially in line with the leaflet gripping elements, but radially inward from them and thus within the convergent capture zone, the clinician may capture a leaflet such that the leaflet gripping element forces the leaflet to cover or occlude a pressure sensing port. This produces a clear and noticeable change in the pressure signal monitored, for example a "flat line" pressure signal. In this way it may be possible to confirm that successful leaflet capture has taken place. Furthermore, it will be appreciated that the parallel lumens may function completely independently of each other such that pressure measurements for each sensing port may be measured independently. This will permit monitoring the pressure signal for each leaflet gripping element individually and thus obtain a "flat line" pressure signal for the first capture leaflet and then thereafter for the second or subsequent captured leaflet.

On the other hand and as described above, the lumens and ports may also be used as suction or vacuum ports. In this case, when the pressure sensing ports are not occluded by a valve leaflet, continuous suction is required to produce a vacuum within the one or more lumens. However, once the pressure port is occluded by a valve leaflet, a vacuum may be produced and maintained within a parallel lumen requiring reduced suction. Thus, by monitoring the suction required to produce a certain pressure within a lumen or by monitoring the pressure within a lumen with a constant suction applied, a noticeable change in feedback signal may be produced when a leaflet has been successfully captured.

Figure 28:
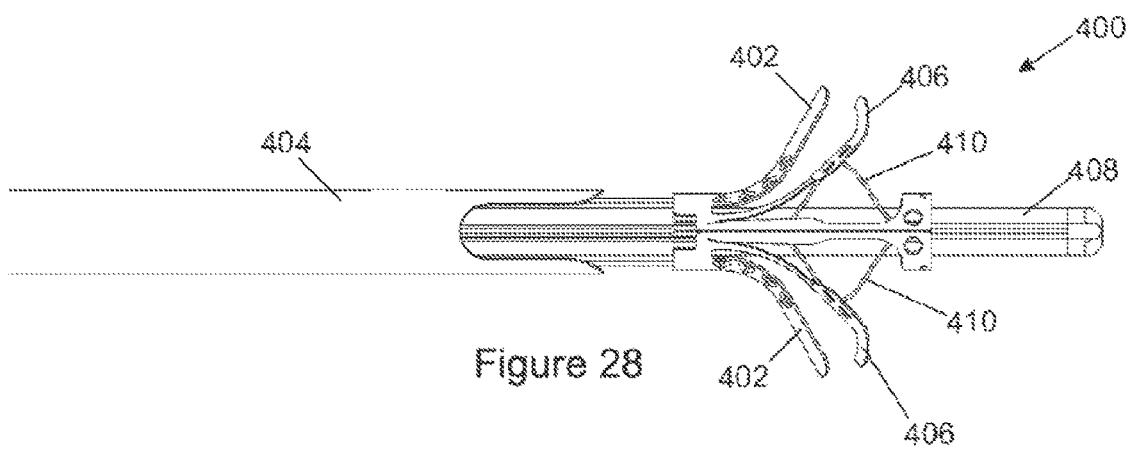
FIG. 28 is a side view of a further embodiment of a heart valve leaflet capture device in which the device includes two atrial stoppers each of which is associated with a leaflet gripping element.

FIG. 28 illustrates still a further embodiment of a leaflet capture device (400) in accordance with the invention. Similar to the embodiment illustrated in FIGS. 20 to 21, the two leaflet gripping elements (402) have a natural capture position and may be moved against the natural bias from the capture position toward their retracted position by means of a longitudinally movable outer sheath (404). In addition, the device (400) further includes two atrial stoppers (406), each being associated with a cooperating leaflet gripping element (402) and which locate between the leaflet gripping elements (402) and the transvalve element (408). The stoppers (406) are individually movable between an inoperative configuration, in which the stopper (406) locates generally adjacent the transvalve element (408), and an operative configuration, in which the stopper (406) diverges outwardly at an acute angle from the transvalve element, as shown in FIG. 28. Movement of the stoppers (406) between the operative and inoperative configuration is enabled through operation of an associated operating mechanism, which in this embodiment comprises a pair of longitudinally movable operating members (410). The operating members (410) are capable of bending laterally so as to move the associated stopper (406) between its inoperative configuration to its operative configuration.

Figure 29:
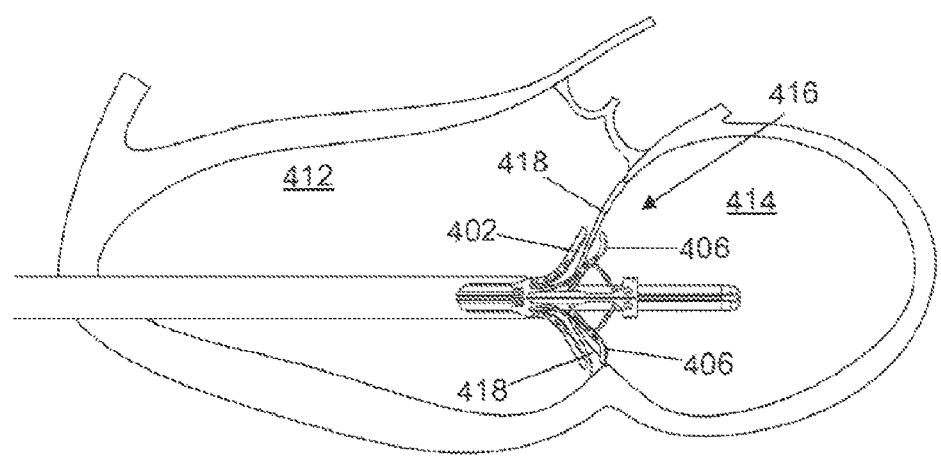
FIG. 29 is a diagrammatic sectional view of the human heart showing the device of FIG. 28 being used to capture the mitral valve leaflets, with the leaflet gripping elements and atrial stoppers in the capture position and operative configuration respectively.
Figure 30:
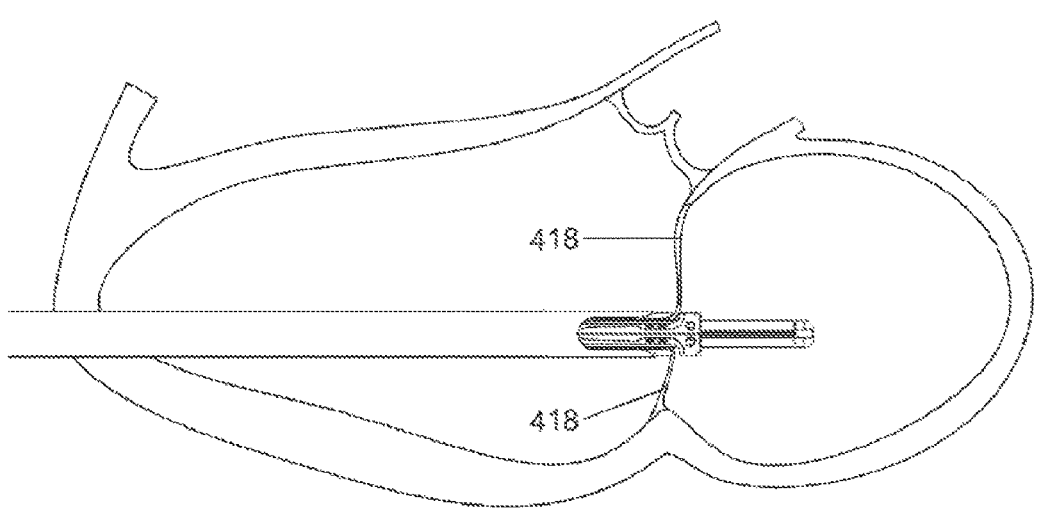
FIG. 30 is a diagrammatic sectional view of the human heart showing the device of FIG. 28 being used to capture the mitral valve leaflets, with the leaflet gripping elements and atrial stoppers in the retracted position and inoperative configuration respectively.
Figure 31:
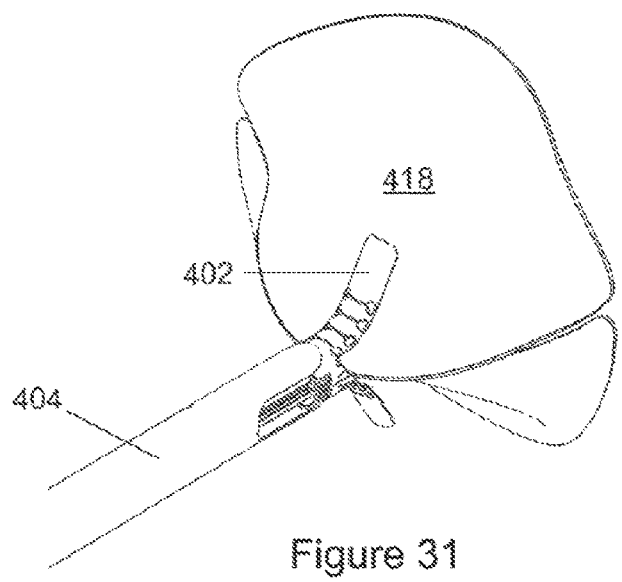
FIG. 31 is a three-dimensional view from the anterior and proximal side of the device shown in FIG. 28 in which the device is being used to capture two valve leaflets.
Figure 32:
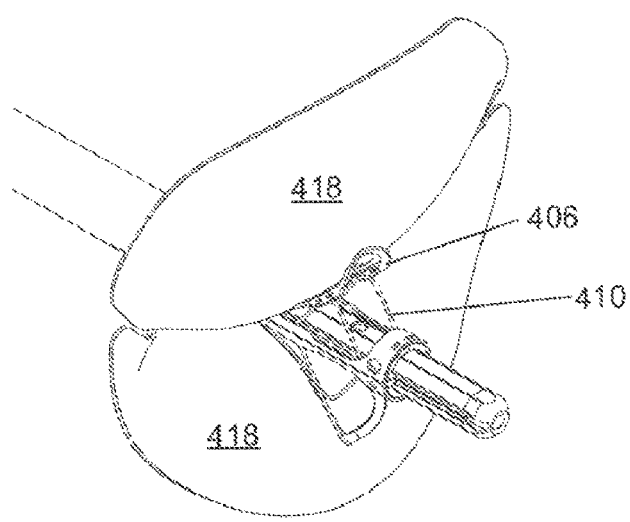
FIG. 32 is a three-dimensional view from the posterior and distal side of the device shown in FIG. 31.
Figure 33:
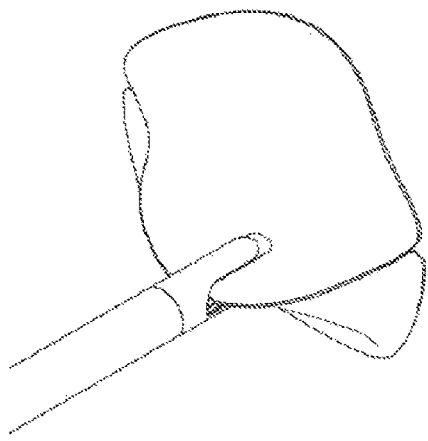
FIG. 33 is a three-dimensional view from the anterior and proximal side of the device shown in FIG. 31 in which the leaflet gripping elements and atrial stoppers in the retracted position and inoperative configuration respectively, with the outer sheath advanced.
Figure 34:
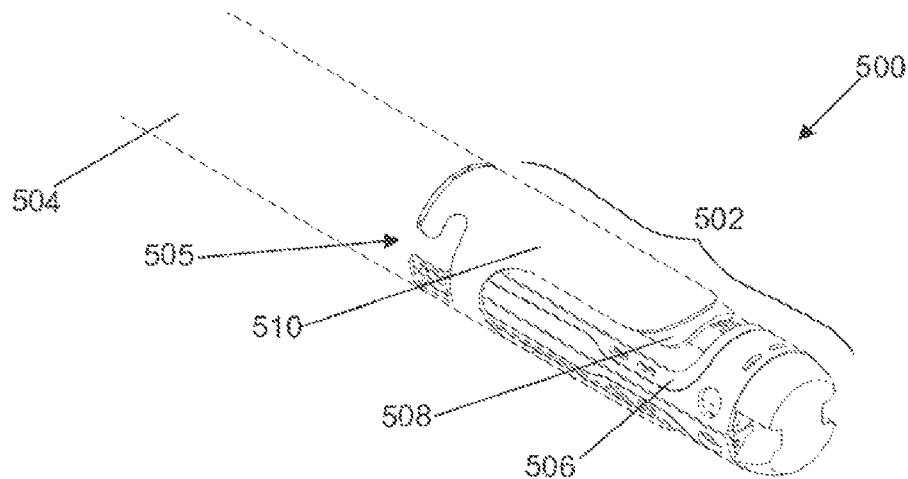
FIG. 34 is a three-dimensional view from the posterior and distal side of a further embodiment of a heart valve leaflet capture device in which the transvalve element is disengageable from the catheter probe so as to fix captured leaflets relative to one another.
Figure 35:
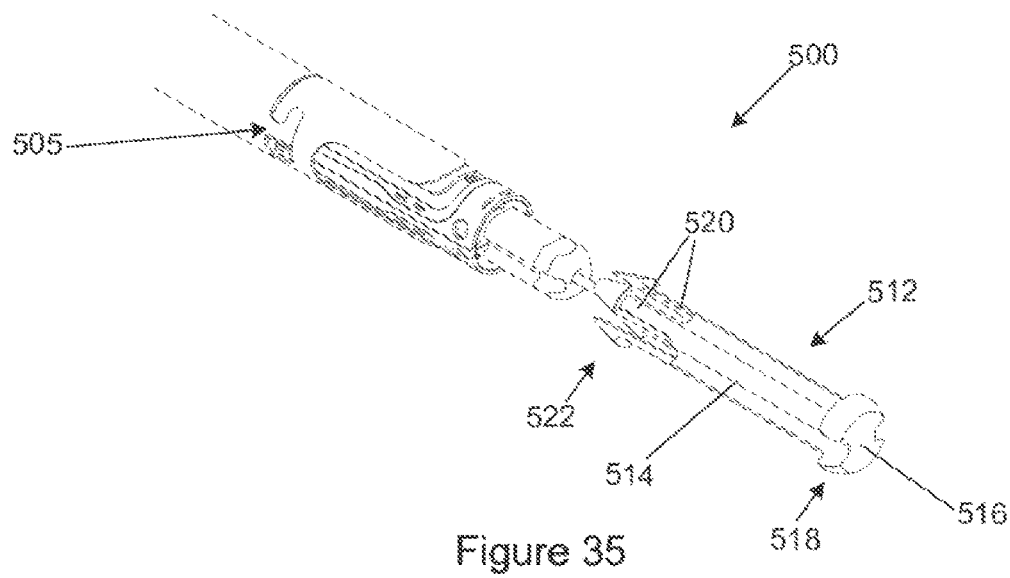
FIG. 35 is a partial exploded view of the device shown in FIG. 34 showing the repair pin separate from the transvalve element.
Figure 36:
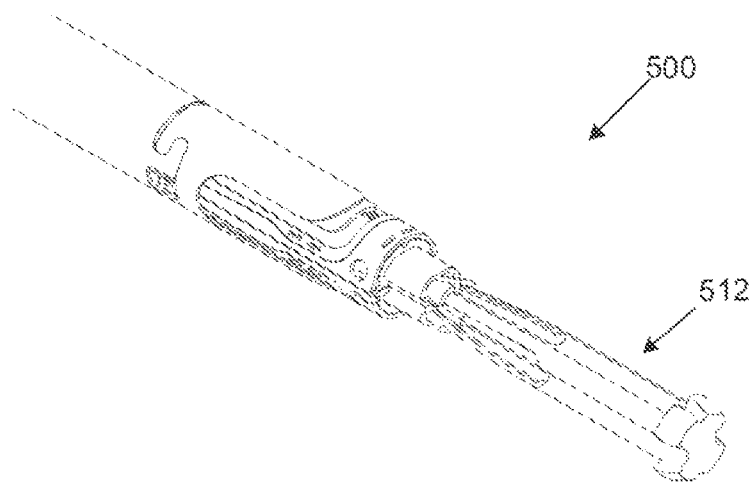
FIG. 36 is a partially exploded view of the device showing the repair pin partially inserted into the transvalve element

In use, and as illustrated in FIGS. 29 to 30 when used in a retrograde procedure, the device (400) is advanced through the ventricle (412) and into the left atrium (414) until the transvalve element (408) locates within the mitral valve (416). At this stage, the outer sheath (404) is withdrawn axially causing the leaflet gripping elements (402) to move to their capture position. Once the position of a leaflet (418) with respect to the leaflet gripping element (402) is determined, for example by means of pressure sensors as described above, and it is determined that the leaflet (418) is within the convergent capture zone defined by the leaflet gripping element (402) when in the capture position, then the atrial stopper (406) is moved into the operative configuration so as to sandwich the leaflet (418) between the leaflet gripping element (402) and the cooperating stopper (406). This is best illustrated in FIGS. 31 and 32. Once both leaflets (418) have been captured, the outer sheath (404) is again advanced, as illustrated in FIG. 33, while at the same time moving the atrial stoppers (406) into their inoperative configuration through collapsing the longitudinally movable operating members (410). This enables the leaflets (418) to be securely captured and held in place between both the leaflet gripping elements (402) and the outer sheath (404) and the transvalve element (408). In addition, this enables the leaflets (418) to be pulled toward each other thereby shortening the septo-lateral distance and correcting annular dilation.

It will of course be appreciated that instead of using the longitudinally movable operating members (410) to move the stoppers (406) between the operative and inoperative configurations, the stoppers may also be configured to naturally adopt the operative configuration, similar to the leaflet gripping elements. In such a case, the stoppers may be movable to the inoperative configuration through a flexible tension element, such as a pull wire, cord, cable or the like. In such a case, the stoppers would be held in the inoperative configuration by means of the tension element until it is determined that the leaflet is located within the convergent capture zone. Once determined, the tension on the tension element is released causing the element move to the operative configuration and to capture the leaflet between the gripping element and the stopper.

In addition, the stoppers may also be movable axially, for example by making use of sliders or the like as shown in FIGS. 17 to 19. The sliders will enable the leaflets to be aligned baso-apically prior to advancing the outer sheath. Alignment of the leaflets may of course also take place once the outer sheath has been advanced, in which case the outer sheath will also be split into two half sheaths.

FIGS. 34 to 42 illustrate yet a further embodiment of a leaflet capture device (500) in accordance with the invention. The device (500) is substantially similar to the device (400) illustrated in FIG. 28, provided that in this embodiment, the device (500) is capable of fixing two or more captured leaflets relative to one another thereby effecting an edge to edge type of repair procedure. In the embodiment illustrated, the transvalve element (502) is disengageable from the catheter probe (504) and remains in position within the heart so as to fix the captured valve leaflets relative to one another. In the embodiment illustrated, the probe (504) and transvalve element (502) are connected to each other by means of a bayonet type fitting (505), however, any other suitable means such as screw threading, a frangible connection or releasable tie cables or wires may also be used.

Figure 38:
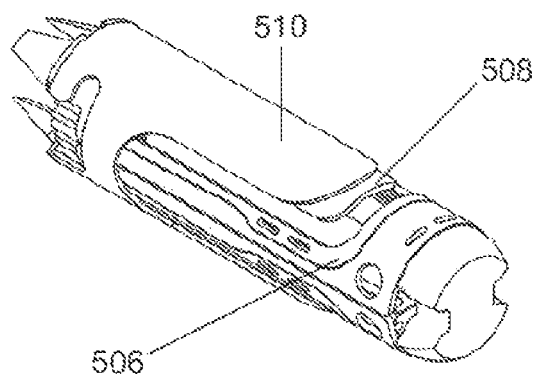
FIG. 38 is a three-dimensional view from the posterior and distal side of the disengaged transvalve element.
Figure 39:
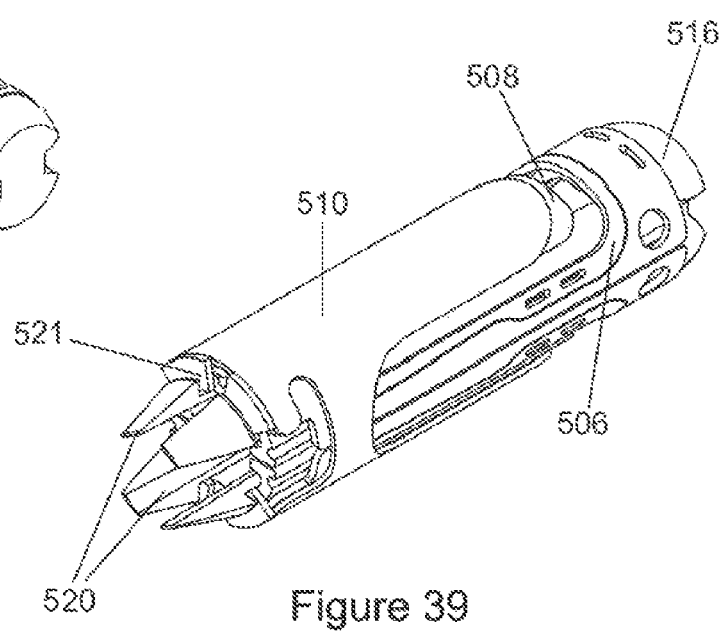
FIG. 39 is a three-dimensional view from the anterior and proximal side of the disengaged transvalve element.

The device (500) again includes two atrial stoppers (506), two leaflet gripping elements (508) as well as an outer sheath (510). In addition, the device (500) includes a repair pin (512) which spans the length of the transvalve element (502) and which is configured to securely retain the atrial stoppers (506), leaflet gripping elements (508) and outer sheath (510) in place once the transvalve element (502) has been disengaged from the catheter probe (504). In the embodiment illustrated, the repair pin (512) comprises a body (514) having a head (516) at one end (518) with a set of feet (520), in this embodiment four, provided at the opposite end (522). The feet (520) are resiliently flexible and have a sloped profile so as to enable them to deflect inwardly thereby permitting the repair pin (512) to be inserted into the transvalve element (502). During disengagement of the transvalve element (502) from the probe (504), the repair pin (512) is withdrawn which causes the feet (520) to move outwardly and engage a shoulder (521) at the proximal end of the transvalve element (502) in a snap fit engagement so as to essentially sandwich together and retain the atrial stoppers (506), leaflet gripping elements (508) and outer sheath (510) in place, as best illustrated in FIGS. 38 and 39. The repair pin (512), and particularly the feet (520) have a profile similar to that of the catheter or probe so as to engage the rails on which the atrial stoppers and leaflet gripping elements are secured.

Figure 37A:
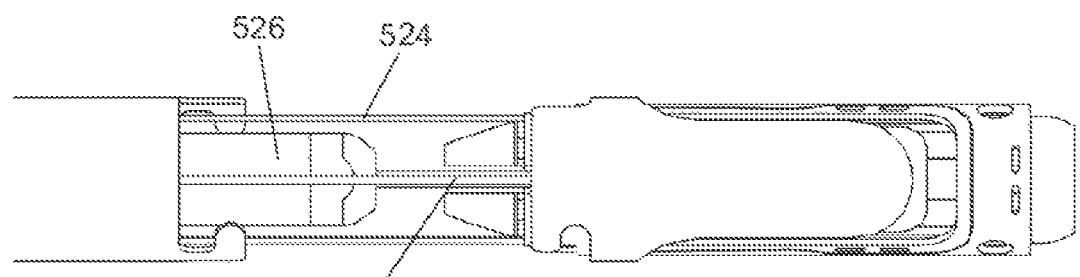
Figure 37C:
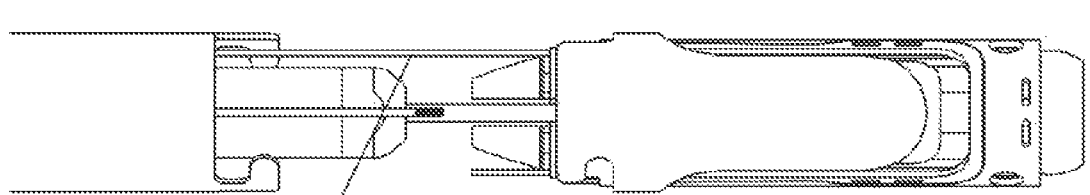
Figure 37C:
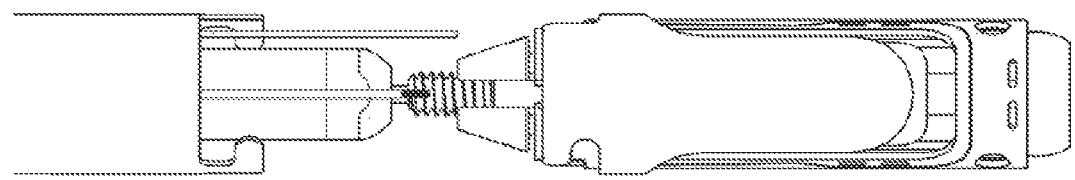

FIGS. 37A to 37C illustrate the procedure of disengaging the probe (504) from the transvalve element (502). This includes disengagement of the leaflet gripping elements actuating mechanism (522), the operating mechanism (524) for operation of the atrial stoppers as well as removal of the pressure probe (526) or the like. Finally, the attachment to the repair pin is removed, at which stage the transvalve element has been fully disengaged and the probe can be removed from the heart.

In this regard, FIGS. 40 to 42 illustrate how the transvalve element (502) remains within the heart after disengagement and removal of the probe. As will be apparent to a person skilled in the art, the transvalve element (502) effectively joins the mitral valve leaflets (528) at a desired position along the free edge of the leaflets so as to create a "double-orifice" mitral valve that is capable of coapting more effectively with no or minimal regurgitation taking place.

Figure 43:
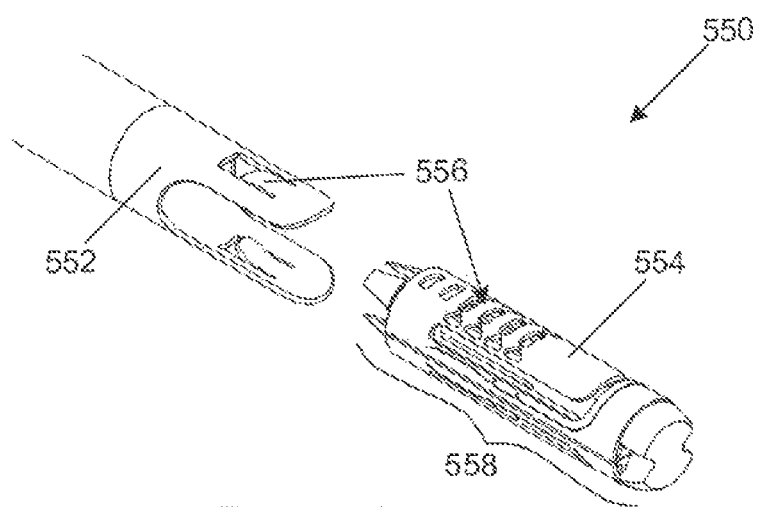
FIG. 43 is a partially exploded view from the posterior and distal side of a further embodiment of a heart valve leaflet capture device in which the outer sheath and leaflet gripping formations include complementary attachment formations to secure the outer sheath to the transvalve element.
Figure 44:
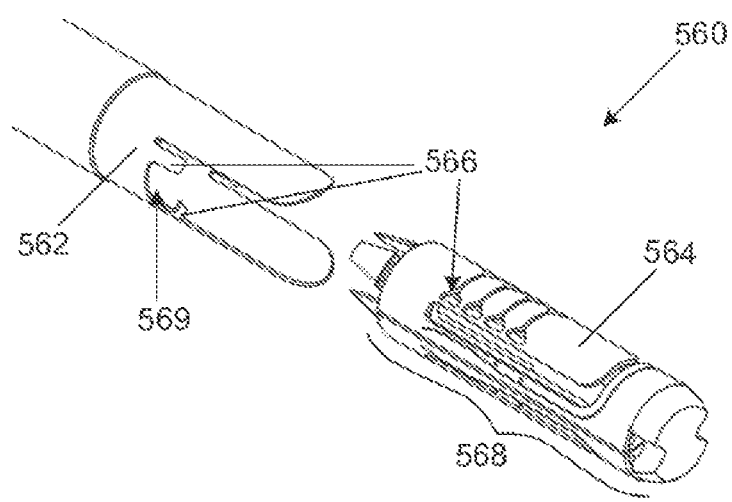
FIG. 44 is a partially exploded view from the posterior and distal side of a further embodiment of a heart valve leaflet capture device in which the outer sheath and leaflet gripping formations include complementary attachment formations.
Figure 45:
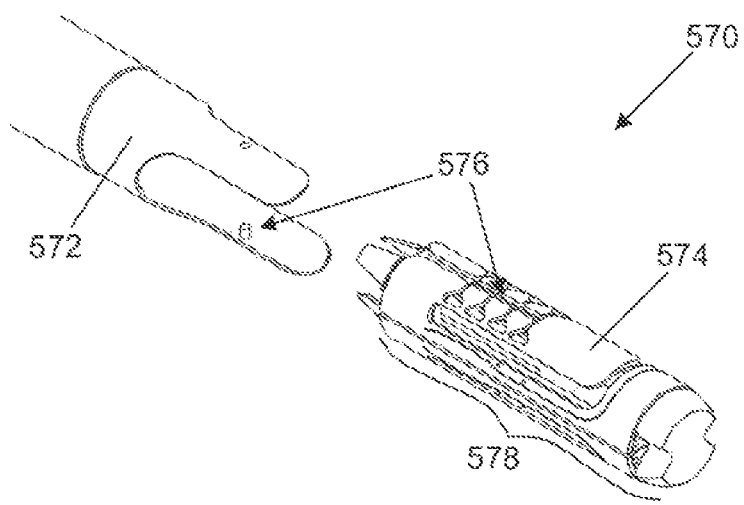
FIG. 45 is a partially exploded view from the posterior and distal side of a further embodiment of a heart valve leaflet capture device in which the outer sheath and leaflet gripping formations include complementary attachment formations.

FIGS. 43 to 45 illustrated three further embodiments of a leaflet capture device (550, 560, 570) in accordance with the invention. The devices (550, 560, 570) are substantially similar to the device (500) illustrated in FIGS. 34 to 44, provided that in these embodiments, the outer sheath (552, 562, 572) and leaflet gripping elements (554, 564, 574) include complementary attachment formations (556, 566, 576) which secure the outer sheath (552, 562, 572) to the leaflet gripping elements (554, 564, 574) thereby retaining the transvalve element (558, 568, 578) in its retracted position after disengagement. In this regard, in the embodiment illustrated in FIG. 43, the complementary attachment formations (556) are in the form of a ratchet tabs cut out from the outer sheath (552) with a series of recesses provided in the outer surface of the leaflet gripping elements (554). It will be appreciated that once the outer sheath (552) has been sufficiently advanced such that the ratchet tabs engage with the recesses, movement of the outer sheath (552) in the opposite direction will be substantially prevented. Similarly, the device (560) illustrated in FIG. 44 includes two ratchet tabs provided in the cut outs (569) of the outer sheath (562) and which are configured to engage with any one of a series of recesses provided in the leaflet gripping elements (564). In still a further embodiment and as illustrated in FIG. 45, instead of making use of a ratchet tabs and recesses, the device (570) makes use of a bayonet type complementary attachment formations (576) which include two pins that extend inwardly from the outer sheath (572) and which are configured to engage with one of a series of slots provided on the leaflet gripping elements (574). It will of course be appreciated that many more embodiments of suitable attachment formations exist.

Figure 46:
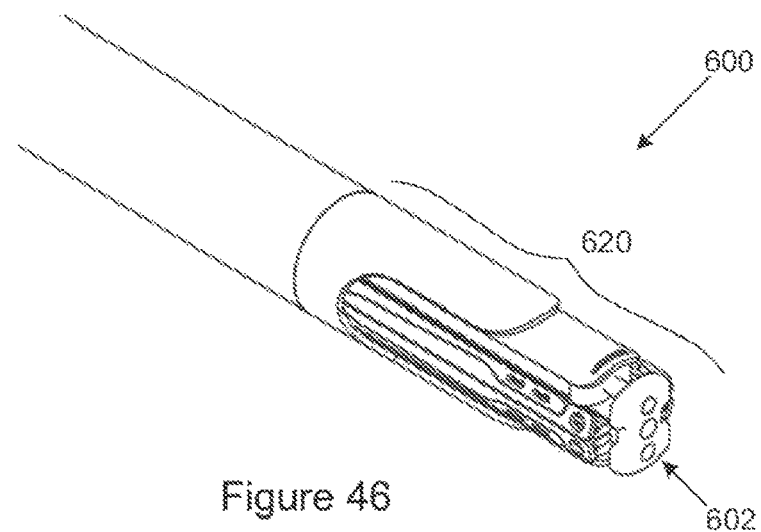
FIG. 46 is a three-dimensional view from the posterior and distal side of a further embodiment of a heart valve leaflet capture device in which the device includes a piercing element so as to pierce captured leaflets and fix them relative to one another.
Figure 47:
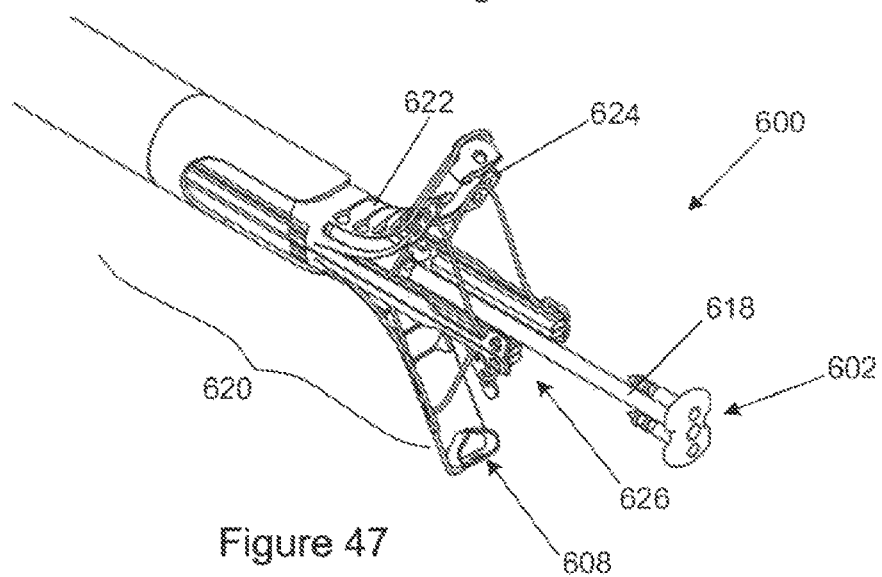
FIG. 47 is the device shown in FIG. 46 in which the leaflet gripping elements and atrial stoppers are in the capture position and operative configuration respectively, with the locking members secured to the leaflet gripping elements and the piercing element moved distally of the transvalve element.
Figure 48:
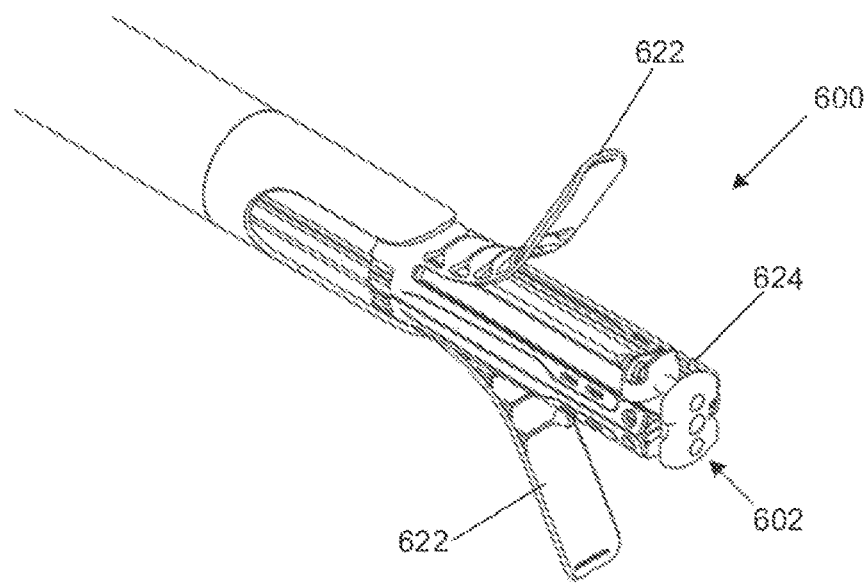
FIG. 48 is the device shown in FIGS. 46 and 47 in which the atrial stoppers are in the inoperative configuration with the leaflet gripping elements in their capture position with the piercing members of the piercing element engaging the locking members.
Figure 49A:
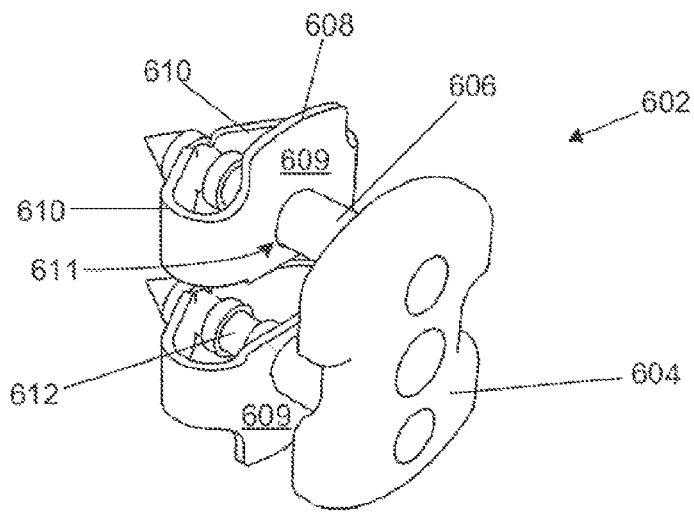
FIG. 49 is a three-dimensional view of one embodiment of a piercing element and locking members to be used with the device shown in FIGS. 46 to 48.
Figure 50:
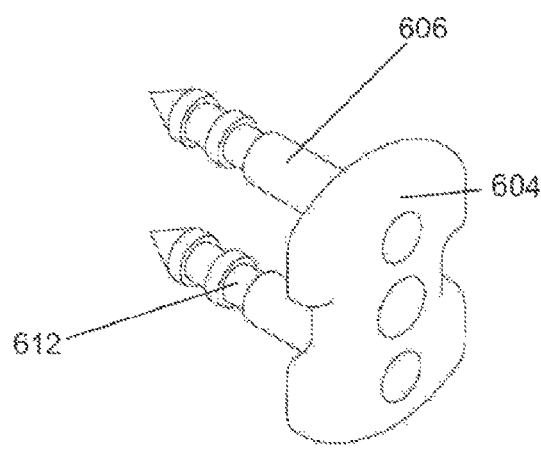
FIG. 50 is a three-dimensional view of the piercing element shown in FIG. 49.
Figure 51:
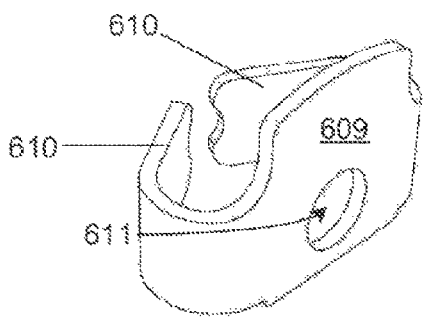
FIG. 51 is a three-dimensional view of a locking member shown in FIG. 49.
Figure 53:
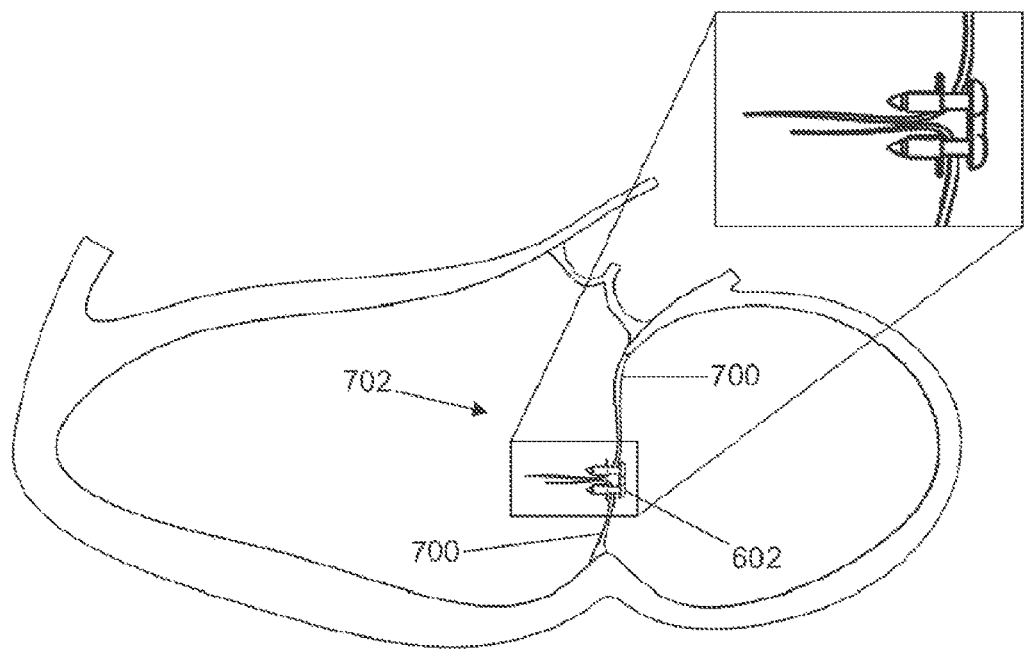
FIG. 53 is a diagrammatic sectional view of the human heart showing the piercing element shown in FIG. 49 being used to fix the two mitral valve leaflets relative to one another.

FIGS. 46 to 48 illustrate yet a further embodiment of a leaflet capture device (600) in accordance with the invention. Similar to the device (500) illustrated in FIGS. 34 to 42, the device (600) of this embodiment is also capable of fixing two or more captured leaflets relative to one another so as to affect an edge to edge type of repair procedure, however, in this embodiment the device (600) fixes the leaflets relative to one another by means of a piercing element (602). As best illustrated in FIGS. 49 and 50, the piercing element (602) comprises a base (604) from which extend two piercing members (606) that are configured to pierce captured leaflets and retain them relative to one another, as will be described in more detail further below. In addition, the piercing element (602) further includes a pair of locking members (608), one of which is illustrated in FIG. 51, and each of which comprises a body (609) from which extend, on diametrically opposite sides, two inwardly bent locking tabs (610). Each body (609) includes a central aperture (611) to receive a piercing member (606) therethrough once a leaflet has been pierced. The locking tabs (610) are shaped and configured to engage with cooperating circumferential grooves (612) provided along the length of the piercing members (606) so as to retain the locking member (608) spaced apart from the base (604) of the piercing element (602). In this way, once a leaflet has been captured, the piercing members (606) are advanced into the apertures (611) provided in the body (609) of the locking members (608) thereby sandwiching the leaflet between the locking member (608) and the base (604) of the piercing element (602), as best illustrated in FIGS. 53 and 54. Once sufficiently advanced through the apertures (611), the locking tabs (610) engage with the circumferential grooves (612) in a ratchet-type manner so as to retain the locking member (608) in place and prevent its removal. It will be appreciated that since each piercing member (606) includes more than one circumferential groove (612) with which the locking tabs (610) can engage, the piercing element (602) can accommodate varying leaflet thicknesses. In addition, by sandwiching the leaflet between the base (604) and the body (609) of the locking members (608), the force on the leaflets is distributed over a larger area thereby minimizing the risk of the piercing element (602) being torn out from the leaflet.

As illustrated in FIG. 47, the piercing element (602) is suspended from a central rod (618) and held housed within the transvalve element (620) during insertion of the device (600) into the heart and when the leaflet gripping elements (622) and the atrial stoppers (624) are in the retracted position and inoperative configuration, respectively. The central rod (618) is axially movable so as to enable movement of the piercing element (602) away from or toward the distal end (626) of the transvalve element (620) during capture and fixation of the leaflets. Furthermore, and as illustrated in FIG. 47, the locking members (608) are removably secured to the leaflet gripping elements (622) and thus move with the leaflet gripping elements (622) during movement thereof from the retracted to the capture position. Prior to leaflet capture, the central rod (618) which holds the piercing element (602) is advanced so as to move the piercing element (602) away from the distal end (626) of the transvalve element (620). Once the leaflets have been captured, as described above with reference to FIGS. 28 to 33, the atrial stoppers (624) and leaflet gripping elements (622) are returned to their inoperative configuration and retracted position respectively. By returning leaflet gripping elements (622) to their retracted position, the apertures (611) in the body (609) of the locking members (608) are aligned with the piercing members (606). Movement of the central rod (618) in the opposite direction, causes the piercing member (602) to be moved toward the distal end (626) of the transvalve element (620) and subsequent piercing of the captured leaflets. In addition, since the apertures (611) of the locking members (608) are aligned with the piercing members (606), the piercing members (606) advance into the apertures (611) subsequently causing the locking tabs (610) to engage with the circumferential grooves (612) and thereby locking and/or retaining the locking members (608) on the piercing members (606).

Figure 52:
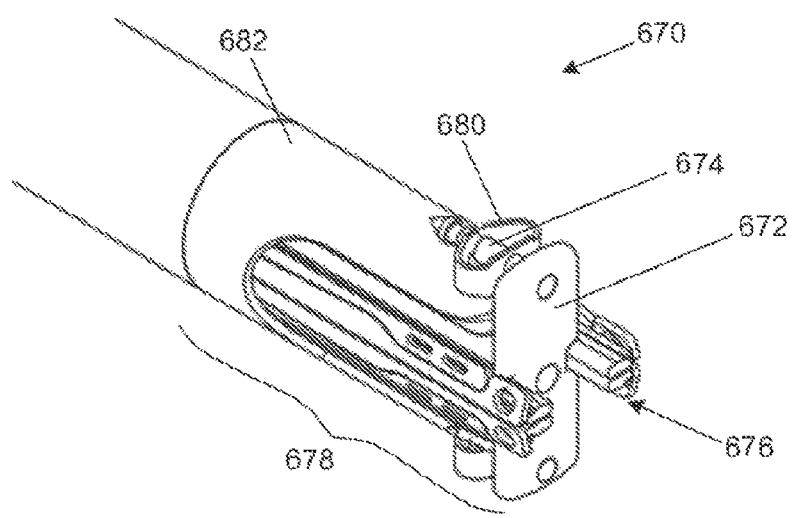
FIG. 52 is an alternative embodiment of a heart valve leaflet capture device which includes a piercing element to pierce captured leaflets, in which the piercing members located radially outside of the distal end of the device.

FIG. 52 illustrates an alternative embodiment of a leaflet capture device (670) in accordance with the invention. The device (670) is substantially similar to the device (600) illustrated in FIGS. 46 to 48, provided that in this embodiment, the piercing element (672) is dimensioned such that the piercing members (674) thereof located radially outside of the distal end (676) of the transvalve element (678). In this embodiment, the locking members (680) may be releasably secured to the outer sheath (682) so as to align the locking members (680) with the piercing members (674) once the leaflets have been captured and the outer sheath (682) has been advanced.

Figure 54A:
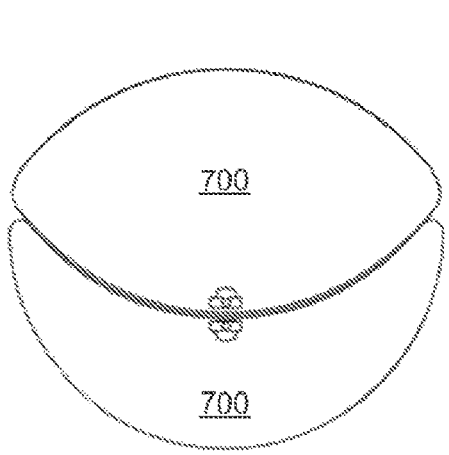
FIG. 54A to 54C are a series of anterior and posterior views of the mitral valve leaflets in which the piercing element shown in FIG. 49 is used to fix the two leaflets relative to one another.
Figure 54B:
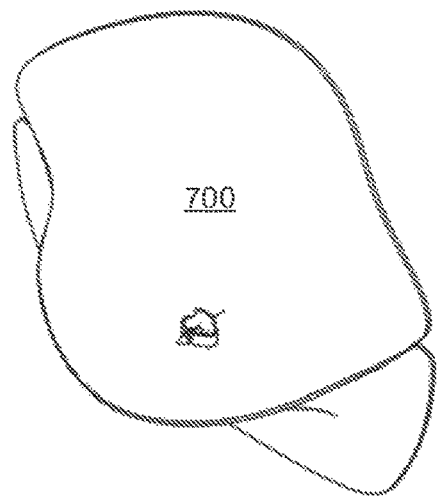
Figure 54C:
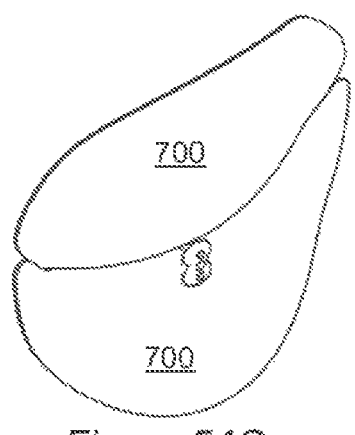

FIGS. 54A to 54C illustrate various views of the piercing element (602) of FIG. 49 used to fix the two leaflets (700) of the mitral valve (702) relative to one another. It will of course be appreciated that a piercing element (602) may have more than two piercing members (606) so as to have two or more piercing members (606) piercing one leaflet (700).

In addition, pressure sensing ports connected to lumens may be provided at leaflet gripping element or atrial stopper and which move with the leaflet gripping element or atrial stopper during movement from the retracted condition to the capture position or from the inoperative configuration to the operative configuration. By permitting the pressure sensing ports and lumens to move with leaflet gripping elements or atrial stoppers, successful leaflet capture may be determined while the leaflet gripping elements and atrial stoppers are in the capture position and operative configuration respectively. In this way, the leaflet gripping elements may remain in the capture position until a leaflet is successfully captured between the leaflet gripping element and the atrial stopper prior to moving them back to the retracted position and inoperative configuration respectively and advancing the outer sheath.

It will be appreciated that many other leaflet capture devices exist which fall within the scope of the invention, particularly as regards the shape, configuration and operation thereof. For example, the leaflet capture confirmation system described with above with reference to FIGS. 20 to 21 and 25 to 27 may in an alternative embodiment make use of optical verification in place of pressure based verification. Here, the principal method described above remains the same, but in place of pressure sensing ports the system would use light sensing ports capable of producing a noticeable change in the displayed signal when a leaflet is successfully captured. Alternatively, the leaflet capture confirmation system may make use of electrical verification in which case electrical signal sensing ports capable of producing a noticeable change in the displayed signal when a leaflet is successfully captured. For example, it may be possible to measure a known electrical signal when a leaflet gripping element in its retracted position contacts an electrical signal sensing port positioned within the convergent capture zone. Once a leaflet is captured between the leaflet gripping element and the transvalve element, the known electrical signal may no longer be detected since the presence of the leaflet would prevent the signal from reaching the transducer or from being received.

Also, the leaflet gripping elements may be configured to be actuated by inflating a balloon thereby forcing the leaflet gripping elements from a natural position to either a capture or a retracted position, as the case may be. This may of course also apply to the atrial stoppers.

In addition, various other embodiments of piercing elements may exist which enable fixing of captured leaflets in a similar manner. For example, instead of the piercing members extending from a base and being advanced into the apertures provided in the locking formations, the base could comprise the locking formation with the piercing elements being releasably secured to the atrial stoppers or outer sheath. In this case, the base would be moved toward the piercing elements causing them to pierce the leaflets and subsequently be received in apertures provided in the base.

It is further envisaged that the leaflet gripping elements, atrial stoppers and other components of the embodiments of the invention described above be made from plate that is laser cut and bent to the required shape or from a laser cut tube. Alternatively, for complex shapes of certain components to be machined; moulded or 3D printed.

Throughout the specification and claims unless the contents requires otherwise the word 'comprise' or variations such as 'comprises' or 'comprising' will be understood to imply the inclusion of a stated integer or group of integers but not the exclusion of any other integer or group of integers.

The invention claimed is:

1. A heart valve leaflet capture device comprising:
a cardiac catheter probe having a proximal end for manipulating the device and a distal end terminating in a transvalve element configured to pass through a heart valve generally parallel to a longitudinal axis of the catheter, and
two or three leaflet gripping elements each of which is movable by operation of an associated actuating mechanism from a radially retracted position to a capture position and from the capture position to the radially retracted position, wherein when in the radially retracted position, the leaflet gripping element is withdrawn with respect to the transvalve element and when in the capture position, the leaflet gripping element diverges outwardly at an acute angle from the transvalve element, wherein the leaflet gripping elements are positioned relative to the transvalve element so that each in its capture position forms a convergent capture zone directed towards the edges of a target valve leaflet, wherein the leaflet gipping elements are movable independently of each other between the capture position and the radially retracted position to enable independent movement of each of the leaflet gripping elements relative to the other leaflet gripping elements, and
wherein two or three atrial stoppers are provided, each being associated with one of the two or three leaflet gripping elements and located between the associated leaflet gripping element and the transvalve element, wherein the atrial stoppers are movable by operation of an associated operating mechanism from an inoperative configuration to an operative configuration and from the operative configuration to the inoperative configuration, wherein when in the inoperative configuration, the atrial stopper locates generally adjacent the transvalve element and when in the operative configuration, the atrial stopper diverges outwardly at an acute angle from the transvalve element so as to enable capturing of a target valve leaflet between the atrial stopper and the associated leaflet gripping element, wherein the atrial stoppers are movable independently of each other and independently of their associated leaflet gripping element such that when a leaflet gripping element is in the capture position, the atrial stopper associated therewith is independently movable between the inoperative configuration and the operative configuration relative to the associated leaflet gripping element or the other atrial stoppers.

2. The device as claimed in claim 1, wherein the leaflet gripping elements actuating mechanism includes longitudinally movable buckling elements that are integrated with an associated leaflet gripping element by virtue of the buckling element being free to buckle laterally to move an associated leaflet gripping element between its radially retracted position and its capture position.

3. The device as claimed in claim 1, wherein the leaflet gripping elements are configured to naturally adopt the capture position in the absence of any forces being applied thereto and for the actuating mechanism to include a longitudinally movable outer sheath which engages the leaflet gripping elements to move them towards their radially retracted positions.

4. The device as claimed in claim 1, wherein the leaflet gripping elements are configured to naturally adopt the capture position in the absence of any forces being applied thereto and for the actuating mechanism to include a flexible tension element to move the leaflet gripping elements towards their radially retracted positions.

5. The device as claimed in claim 1, wherein the leaflet gripping elements are individually pivotally attached to the catheter probe or transvalve element thereof.

6. The device as claimed in claim 1, wherein at least one pressure sensor port is associated with the catheter so that the pressure exerted on the distal end thereof can be monitored for control purposes and as a guide to a clinician carrying out a cardiac procedure using the device.

7. The device as claimed in claim 6, wherein the at least one pressure sensor port is slideably connected or axially movable to enable use thereof for assessing atrio-ventricular position or for assessing leaflet position relative to the device and successful leaflet capture by the leaflet gripping elements of the device.

8. The device as claimed in claim 1, wherein the catheter includes a longitudinal slider associated with each of the leaflet gripping elements and associated atrial stoppers to enable adjusting their positions along the length of the transvalve element or catheter.

9. The device as claimed in claim 1, wherein the catheter and transvalve element are longitudinally split into two or more longitudinally adjustable parts that can be moved in order to adjust the positions of the leaflet gripping elements and their associated atrial stoppers along the length of the transvalve element or catheter to thereby effectively capture heart valve leaflets or to align captured leaflets into a desired relative position.

10. The device as claimed in claim 1, wherein the operating mechanism includes longitudinally movable operating members that are integrated with an associated atrial stopper and which are free to bend laterally so as to move an associated stopper between its inoperative configuration and its operative configuration.

11. The device as claimed in claim 1, wherein each atrial stopper is configured to naturally adopt the operative configuration in the absence of any forces being applied thereto and for the operating mechanism to include a flexible tension element to move the stopper towards its inoperative configuration.

12. The device as claimed in claim 1, wherein each atrial stopper is configured to naturally adopt the inoperative configuration in the absence of any forces being applied thereto and for the operating mechanism to include a flexible tension element to move the stopper member toward its operative configuration.

13. The device as claimed in claim 1, wherein the device includes a piercing element configured to pierce captured leaflets so as to fix the leaflets relative to one another, wherein the piercing element is releasably attached to an axially movable rod at or near the distal end of the transvalve element to enable movement of the piercing element toward or away from the distal end of the transvalve element to enable piercing of captured leaflets.

14. The device as claimed in claim 13, wherein the piercing element comprises a base from which extend two or more piercing members for piercing leaflets and one or more locking members configured to receive the two or more piercing members so as to sandwich captured leaflets between the base and the one or more locking members, wherein each locking member includes two or more inwardly bent locking tabs that are configured to engage in a ratchet-type manner with complementary shaped circumferential grooves provided along the length of each piercing member.

15. The device as claimed in claim 1, wherein the transvalve element is attached to the catheter probe by means of a bayonet type fitting and is disengageable from the catheter probe so as permit disengagement thereof after capture and alignment of the leaflets to thereby fix the leaflets relative to one another.

* * * * *